(12) United States Patent
Feinmark et al.

(10) Patent No.: US 8,309,528 B2
(45) Date of Patent: Nov. 13, 2012

(54) TWO PORE CHANNELS AS REGULATORS OF PROLIFERATION IN CANCER

(75) Inventors: Steven J. Feinmark, Haworth, NJ (US); Richard B. Robinson, Cresskill, NJ (US)

(73) Assignee: The Trustees of Columbia University in the City of New York, New York, NY (US)

( * ) Notice: Subject to any disclaimer, the term of this patent is extended or adjusted under 35 U.S.C. 154(b) by 576 days.

(21) Appl. No.: 12/299,852

(22) PCT Filed: May 9, 2007

(86) PCT No.: PCT/US2007/011339
§ 371 (c)(1),
(2), (4) Date: Jun. 15, 2009

(87) PCT Pub. No.: WO2007/133654
PCT Pub. Date: Nov. 22, 2007

(65) Prior Publication Data
US 2009/0317811 A1    Dec. 24, 2009

Related U.S. Application Data

(60) Provisional application No. 60/799,486, filed on May 10, 2006, provisional application No. 60/835,336, filed on Aug. 2, 2006.

(51) Int. Cl.
*A61K 48/00* (2006.01)
*C07H 21/02* (2006.01)
*C07H 21/04* (2006.01)

(52) U.S. Cl. .................... 514/44 R; 536/23.1; 536/23.5

(58) Field of Classification Search .................. None
See application file for complete search history.

(56) References Cited

U.S. PATENT DOCUMENTS

| 2002/0028485 A1 | 3/2002 | Meadows et al. | |
| 2003/0105000 A1* | 6/2003 | Pero et al. | 514/12 |
| 2006/0019256 A1* | 1/2006 | Clarke et al. | 435/6 |

OTHER PUBLICATIONS

Freshney (Culture of Animal Cells, A Manual of Basic Technique, Alan R. Liss, Inc., 1983, New York, p. 4).*
Dermer (Bio/Technology, 1994, 12:320).*
Tian, J et al. (Physiol Genomics, 2004 17:170-182).*
Zips et al (In vivo, 2005, 19:1-7).*
Gura (Science, 1997, 278:1041-1042).*
Kaiser (Science, 2006, 313: 1370).*
Taber's Cyclopedic Medical Dictionary (1985, F.A. Davis Company, Philadelphia, p. 274).*
Busken, C et al. (Digestive Disease Week Abstracts and Itinerary Planner, 2003, abstract No. 850).*
Krontiris and Capizzi (Internal Medicine, 4th Edition, Editor-in-chief Jay Stein, Elsevier Science, 1994 Chapters 71-72, pp. 699-729).*
Bowie et al (Science, 1990, 247:1306-1310).*
Skolnick et al. (TIBTECH 18:34-39, 2000).*
Ibragimova and Eade (Biophysical Journal, Oct. 1999, vol. 77, pp. 2191-2198).*
Burgess et al (J of Cell Bio. 111:2129-2138, 1990).*
Lazar et al (Molecular and Cellular Biology, 1988, 8:1247-1252) gk.*
AAF89743.1 (GenBank, two-pore domain potassium channel Trek-1, Jun. 13, 2001).*
Heginbotham et al., Biophysical Journal, vol. 66, Apr. 1994, 1061-1067; Mutations in the K+ Channel Signature Sequence.*
Pei et al. PNAS, Jun. 24, 2003 vol. 100 No. 13, 7803-7807 Oncogenic potential of TASK3 (Kcnk9) depends on K_channel function.*

* cited by examiner

*Primary Examiner* — Peter J Reddig
(74) *Attorney, Agent, or Firm* — Evans & Molinelli PLLC; Judith A. Evans

(57) ABSTRACT

The present invention relates to the discovery that two pore K+ channel (2PK) gene expression is increased in tumors and tumor cell lines, especially prostate tumor cells. The present invention encompasses methods for disease diagnosis, drug screening and the treatment of cancer.

2 Claims, 13 Drawing Sheets

A. TREK-1 Current in PC3

Figure 1:
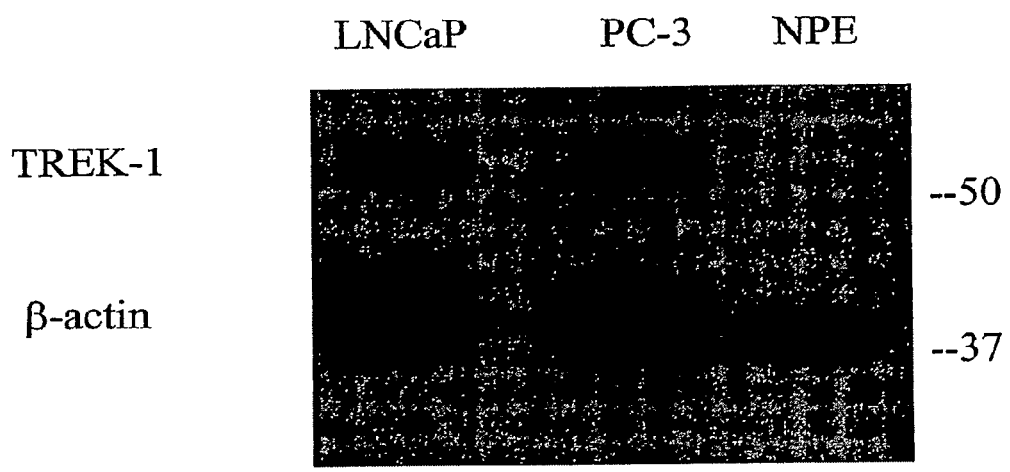

B. TREK-1 Current in PC3 transfected with dnTREK

C. Summary

A. NPE Net Current

B. NPE Current after Infection with adTREK-1

C. Summary

A.

B.

BML264

(ONO-RS-082),

TWO PORE CHANNELS AS REGULATORS OF PROLIFERATION IN CANCER

This application is the national phase (371) application of International application number PCT/2007/011339, filed on May 9, 2007, which claims the benefit of priority to U.S. provisional Application Ser. No. 60/799,486 filed on May 10, 2006, and U.S. provisional Application Ser. No. 60/835,336 filed on Aug. 2, 2006, each of which is incorporated by reference herein in their entirety.

STATEMENT OF GOVERNMENTAL INTEREST

This research was supported under Contract No. W81XWH-06-1-0141 awarded by the Department of Defense. The Government has certain rights in the invention.

1. INTRODUCTION

The present invention relates to the discovery that two pore $K^+$ channel (2PK) gene expression is increased in tumor cell lines, especially prostate tumor cells. The present invention encompasses methods for disease diagnosis, drug screening and the treatment of cancer.

2. BACKGROUND OF INVENTION

Cancer is a disease marked by the uncontrolled growth of abnormal cells. Cancer cells have overcome the natural controls imposed in normal cells, which have a finite lifespan. As the growth of cancer cells continues the cancerous cell may develop a more aggressive growth phenotype. If left untreated, metastasis, the spread of cancer cells to distant areas of the body by way of the lymph system or bloodstream, may ensue, destroying healthy tissue. Carcinoma of the prostate (PCA) is the most frequently diagnosed cancer in men in the United States, and is the second leading cause of male cancer deaths (Karp et al., 1996, Cancer Res. 56:5547-5556).

It would therefore be beneficial to provide methods and reagents for the diagnosis, staging, prognosis, monitoring, and treatment of cancers.

3. SUMMARY OF THE INVENTION

The present invention relates to methods and compositions for modulating the activity of the two-pore domain K+ channels as a means for modulating the proliferation of cancer cells. Specifically, the present invention relates to methods and compositions for modulating the activity of the TREK-1 two-pore domain K+ channels ("TREK-1") as a means for modulating the proliferation of prostate cancer cells. Such modulation can be used to reduce or inhibit the proliferation of prostate tumor cells. The invention is based on the discovery that TREK-1 is over expressed in human prostate cancer cells as compared to normal prostate cells, as well as in breast, colon and bladder cancer cells. Moreover, inhibition of TREK-1 activity was found to inhibit the proliferation of tumor cells.

The present invention further relates to methods for the diagnostic evaluation and prognosis of cancer, especially prostate cancer. For example, TREK-1 nucleic acid molecules can be used as diagnostic hybridization probes or as primers for diagnostic PCR analysis for detection of abnormal levels of expression of the TREK-1 gene. Antibodies to TREK-1 gene product can be used in a diagnostic test to detect the level of TREK-1 gene product in tissue samples. In specific embodiments, measurement of TREK-1 gene product levels can be made to detect or stage cancer, especially prostate cancer.

Still further, the present invention relates to screening assays that utilize the TREK-1 gene and/or TREK-1 gene product for the identification of compounds which modulate TREK-1 gene expression and/or the activity of TREK-1 gene products. In a preferred embodiment of the invention, the compound is one that is capable of inhibiting the activity of TREK-1 and effectively reducing or inhibiting the proliferation of cancer cells. Such compounds can be used as agents to prevent and/or treat cancer. Such compounds can also be used to palliate the symptoms of the disease, and control the metastatic potential of the cancer.

Specifically, the present invention provides a method for identifying a compound that activates TREK-1 activity comprising (i) contacting a cell expressing TREK-1 with a test compound and measuring the level of TREK-1 activity; (ii) in a separate experiment, contacting a cell expressing TREK-1 protein with a vehicle control and measuring the level of TREK-1 activity where the conditions are essentially the same as in part (i), and then (iii) comparing the level of TREK-1 activity measured in part (i) with the level of TREK-1 activity in part (ii), wherein an increased level of TREK-1 activity in the presence of the test compound indicates that the test compound is a TREK-1 activator.

The invention also provides a method for identifying a compound that inhibits TREK-1 activity comprising (i) contacting a cell expressing TREK-1 protein with a test compound and measuring the level of TREK-1 activity, (ii) in a separate experiment, contacting a cell expressing TREK-1 protein with a vehicle control and measuring the level of TREK-1 activity, where the conditions are essentially the same as in part (i) and then (iii) comparing the level of TREK-1 activity measured in part (i) with the level of TREK-1 activity in part (ii), wherein a decrease level of TREK-1 activity in the presence of the test compound indicates that the test compound is a TREK-1 inhibitor.

In yet another embodiment of the invention, a method for identifying a compound that inhibits proliferation of cells expressing TREK-1 activity comprising (i) contacting a cell expressing TREK-1 protein with a test compound and measuring the level of cell proliferation, (ii) in a separate experiment, contacting a cell expressing TREK-1 protein with a vehicle control and measuring the level of cell proliferation, where the conditions are essentially the same as in part (i) and then (iii) comparing the level of cell proliferation measured in part (i) with the level of cell proliferation in part (ii), wherein a decrease level of cell proliferation in the presence of the test compound indicates that the test compound is an inhibitor of cell proliferation.

The invention further provides pharmaceutical compositions comprising a biologically active agent that modulates the activity of TREK-1 in combination with a pharmaceutically acceptable carrier.

4. BRIEF DESCRIPTION OF THE FIGURES

FIG. 1. TREK-1 is expressed in prostate cancer cell lines but not in normal prostate epithelium. Cell lysates were prepared from LNCaP (lane 1), PC-3 (lane 2) and normal prostate epithelial (lane 3) cell cultures and fractionated by SDS-PAGE. The proteins were blotted to nitrocellulose and detected by ECL according to the manufacturer's instructions with a polyclonal rabbit anti-TREK-1 primary antibody (Alomone). Beta-actin was measured as a loading control on the same blots. These results are typical of two experiments.

Figure 2:
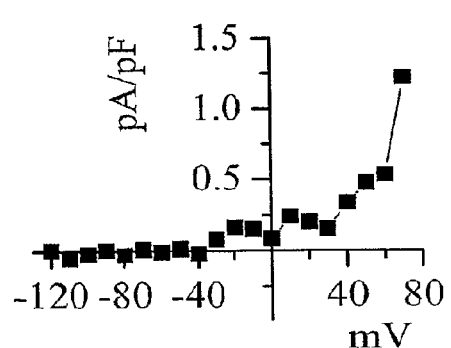
Figure 2:
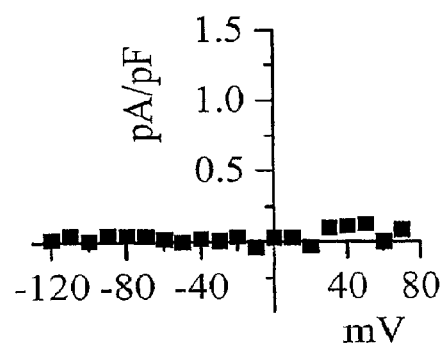
Figure 2:
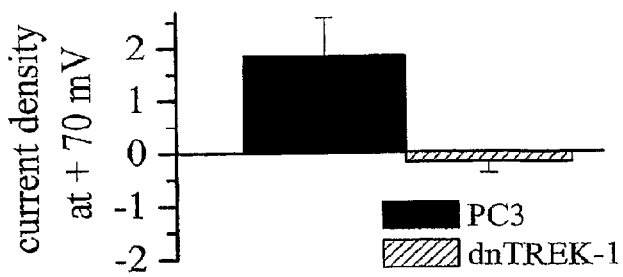

FIG. 2. PC-3 cells express TREK-1 current which can be "knocked-out" by over-expression of a dominant-negative mutant (dn-TREK). Panel A. TREK-1 current is defined as the sipatrigine-sensitive current and is measured using a ramp protocol. A series of 800 ms steps from −120 mV to +70 mV (increasing 10 mV each step) from a holding potential of −20 mV are applied. To eliminate contamination by $Na^+$ current a prestep to −90 mV (40 ms) is applied before each step. Sipatrigine (50 μM) is applied by superfusion for 3 min while recordings are taken every 30 s. The traces reported in the figure are the result of the subtraction of the control current from the current in the presence of sipatrigine at steady state. Panel B. PC-3 cells were co-transfected with dn-TREK and pEGFP-C1 plasmids. 48 h later, dn-TREK cells were identified by green fluorescence and recordings were made as described above. Panel C. Data from numerous cells are summarized in the bar graph.

Figure 3:
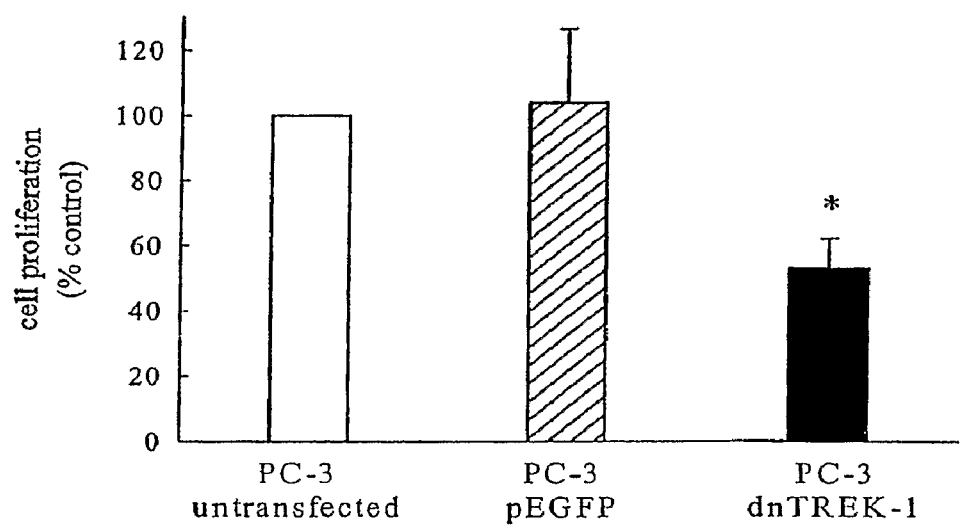

FIG. 3. Dominant-negative TREK-1 reduces proliferation of PC-3 cells. PC-3 cells were transfected with either dn-TREK (or a control vector (PEGFP) using GeneJammer (Stratagene) under standard conditions. Proliferation of these cells was measured using the MTT assay after the cells were plated at $1 \times 10^5$ cells/well in 96 well plates. Data are presented as the mean ±SEM of five experiments. * $p<0.05$ vs control and EGFP FIG. 4. Normal prostate epithelial cells (NPE) express no TREK-1 current but a TREK-1 virus can be used to over-express the channel. Current was measured in cultured NPE by patch-clamp recording as described in FIG. 1. Panel A. TREK-1 current is not detectable in NPE. Panel B. NPE were infected with a TREK-1 bearing adenovirus and current was recorded. Panel C. Summary of numerous trials.

Figure 5:
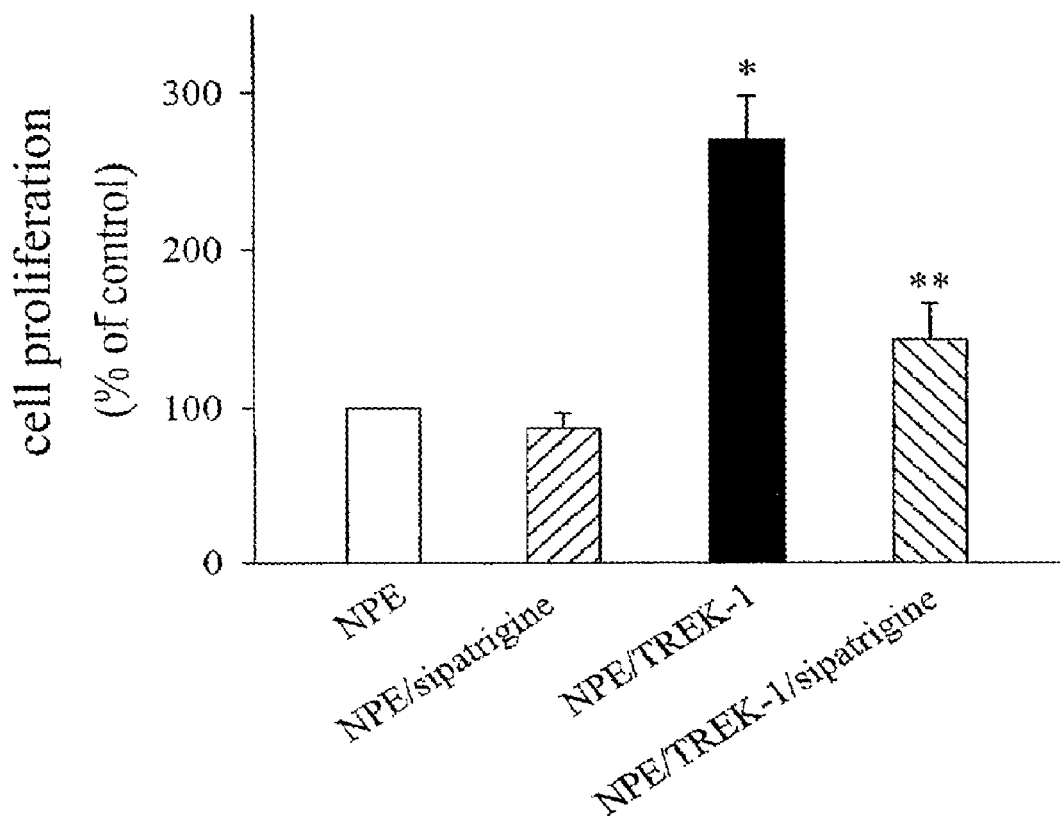

FIG. 5. Expression of TREK-1 increases proliferation of normal prostate epithelial cells (NPE). Normal prostate epithelial cell cultures were obtained from Clonetics and infected with a TREK-1-containing adenovirus. Some virally infected cells were also treated with sipatrigine (10 μM), a TREK-1 blocker. Cell proliferation was assessed using the MTT assay as described in FIG. 3. These data are presented as mean ±SEM from five paired experiments. * $p<0.05$, the NPE/TREK-1 group differed significantly from each of the other treatments and no other groups were different.

Figure 6:
Figure 6:
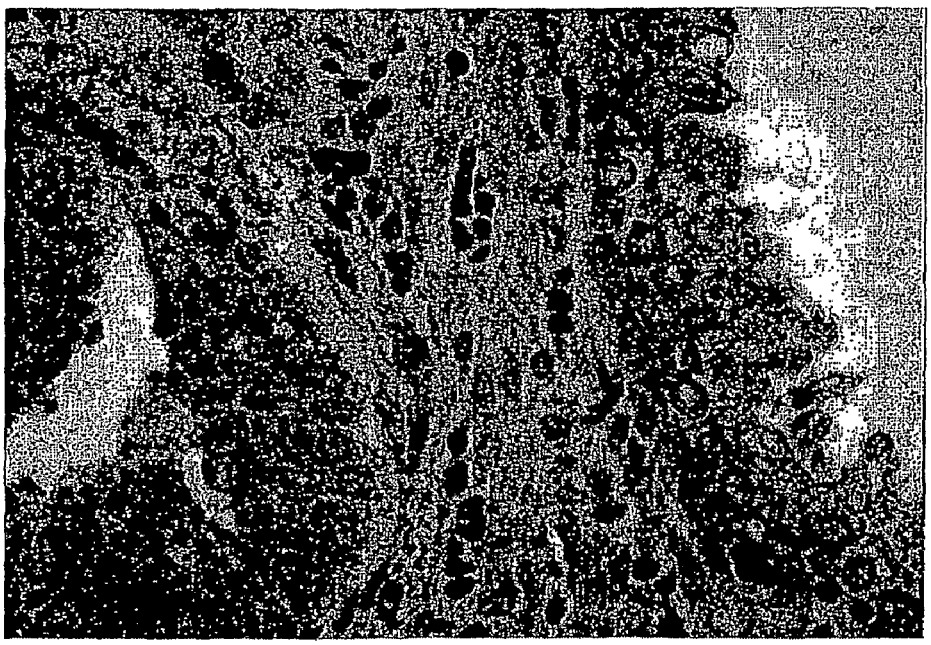

FIG. 6. Immunohistochemical staining of human prostate tissue reveals that TREK-1 is over-expressed in cancer. Human tissue samples were stained with rabbit polyclonal anti-human TREK-1 antibody (Alomone). Panels A and B show a low power and high power view of the same field. Under the low power, a normal gland is visible (center right). The epithelial cells lining the luminal surface are very lightly stained. An adjacent cancerous gland (center left) shows a very small luminal space and the epithelial cells lining it are very densely stained indicating an overexpression of TREK-1. The same features are visible under higher power in Panel B.

Figure 7:
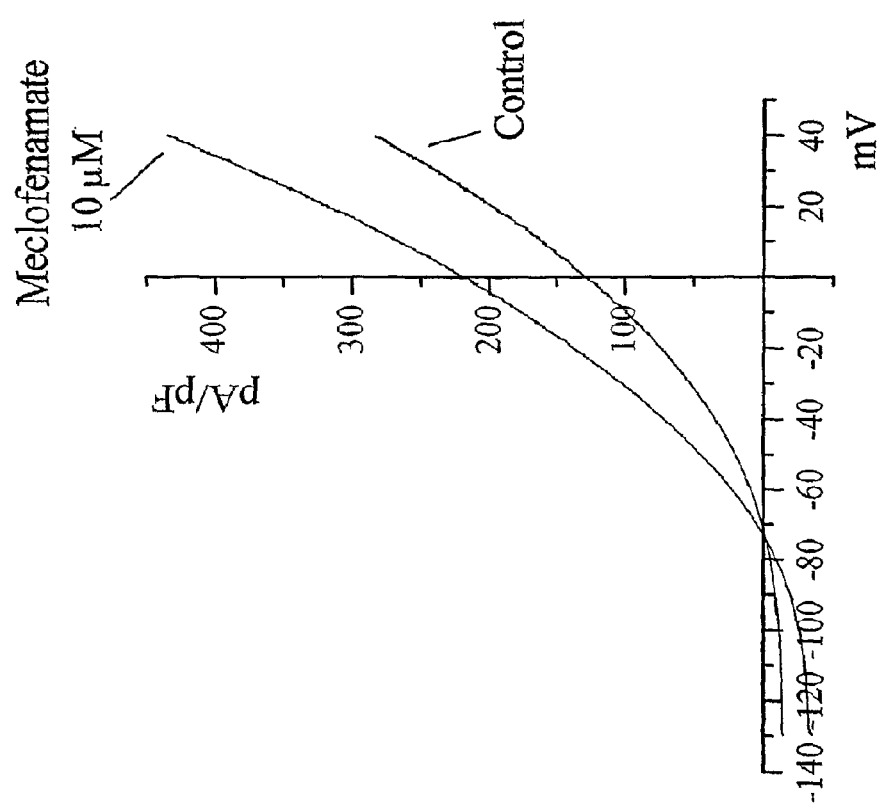

FIG. 7. Meclofenamate activates TREK-1 current in CHO cells that heterologously express the channel. CHO cells were transfected with a plasmid encoding human TREK-1 and the current was studied by patch clamp. The current-voltage relation was determined using a ramp protocol that went from −130 mV to +40 mV in 6 s (after correction for the junction potential). Current was greater in the presence of meclofenamate. This is typical of 7 cells.

Figure 8:
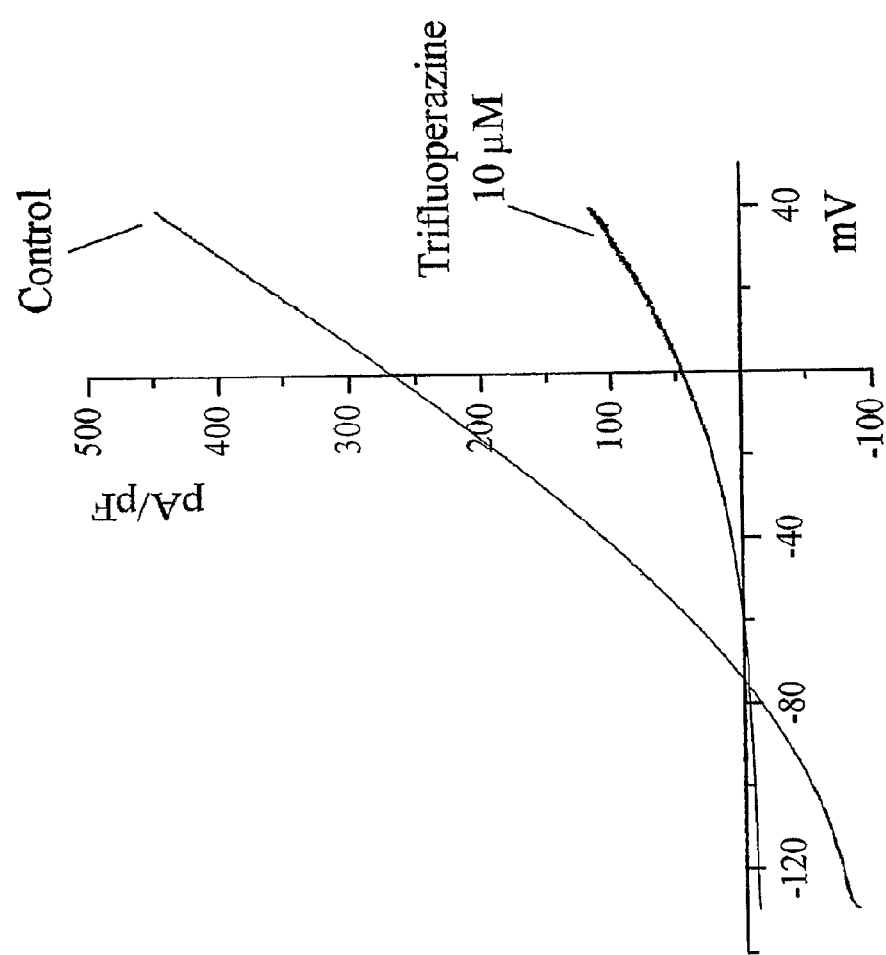

FIG. 8. Trifluoperazine inhibits TREK-1 current in CHO cells that heterologously express the channel. CHO cells were transfected with a plasmid encoding human TREK-1 and the current was studied by patch clamp. The current-voltage relation was determined using a ramp protocol that went from −130 mV to +40 mV in 6 s (after correction for the junction potential). Current was less in the presence of trifluoperazine. This is typical of 3 cells.

Figure 9:
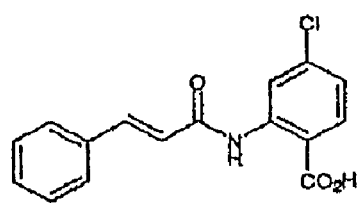
Figure 9:
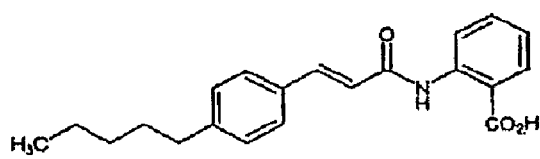
Figure 9:
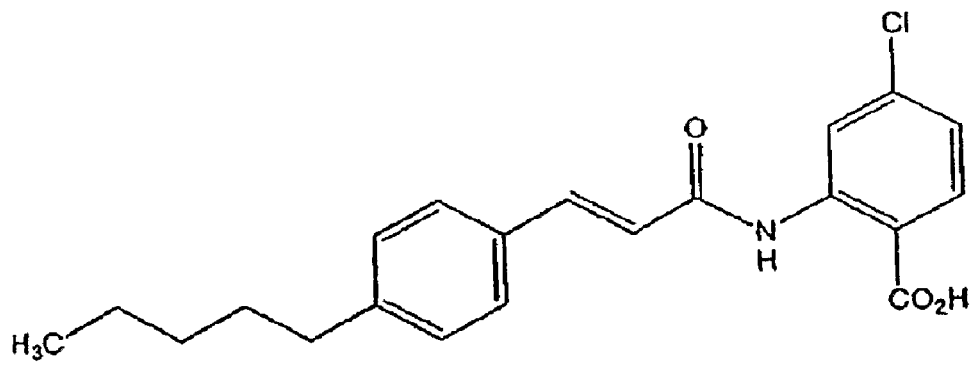

FIG. 9. Structure of ONO-RS-082, BML263 and BLM 264.

Figure 10:
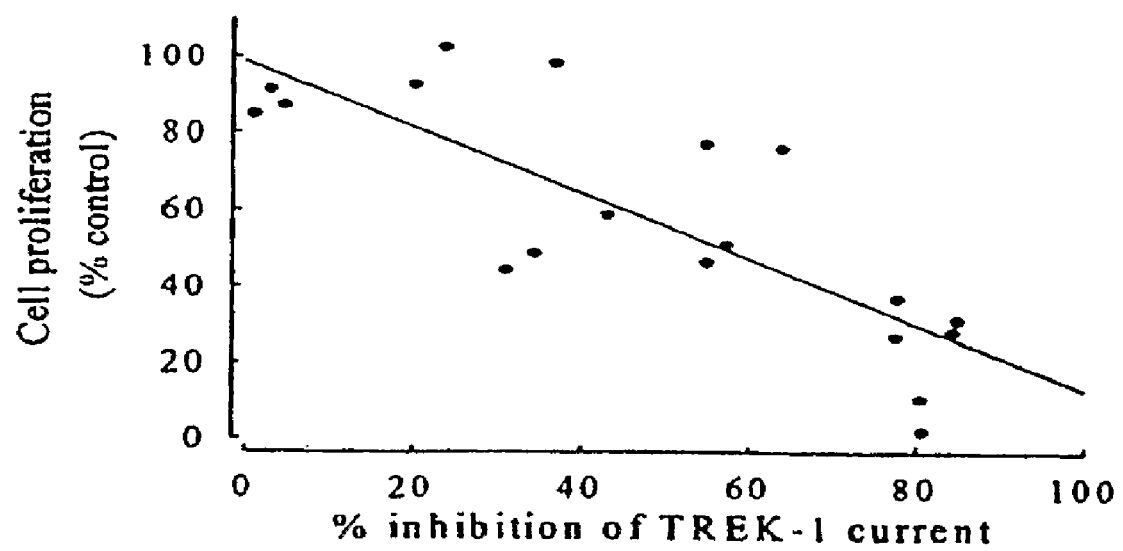

FIG. 10. TREK-1 expression increases proliferation in CHO cells which significantly correlates with current. CHO cells were transfected with TREK-1 using standard methods. Transfected cells were exposed to sipatrigine in doses from 0 to 100 uM and then tested for proliferation and for TREK-1 current by methods described elsewhere in this application. The percent of control proliferation, as measured by the MTT assay, was plotted against the inhibition of TREK-1 current, as measured by patch clamp analysis. The data were then analyzed by linear regression which shows a significant correlation between the rate of growth and the expression of current in these cells ($p<0.0001$).

Figure 11:
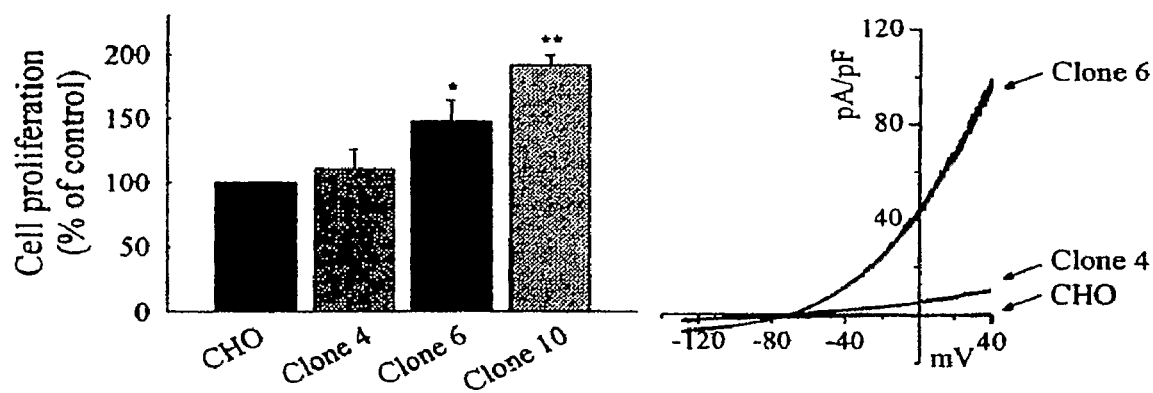

FIG. 11. TREK-1 stable over-expressor cell lines have a significantly higher proliferation rate than control CHO cells. Several clones of CHO cells that over-express TREK-1 have been isolated as described elsewhere. Each clone was tested for the expression of current (right panel) and for its proliferation rate (left panel).

Figure 12:
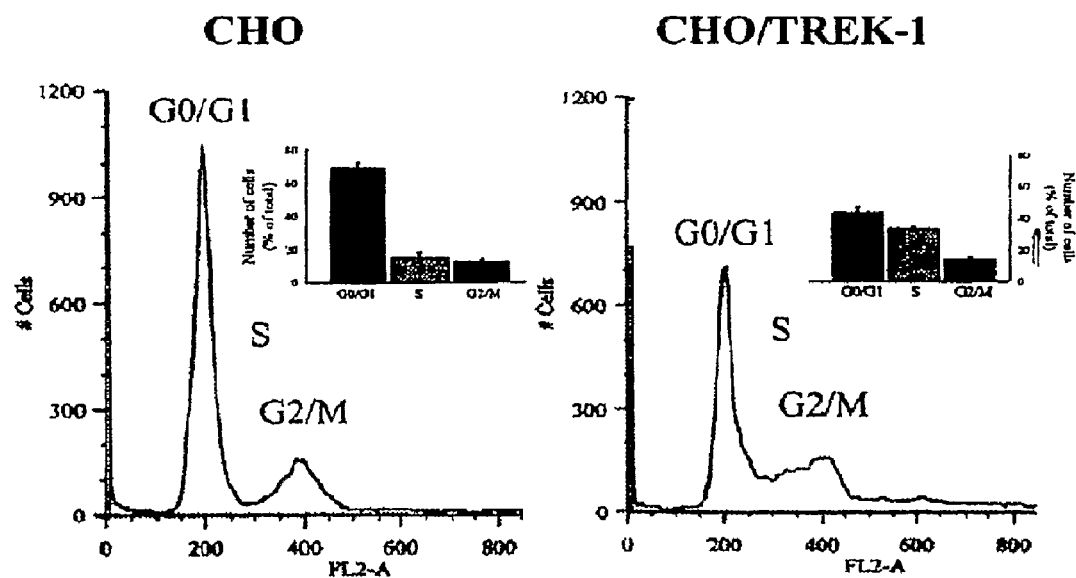

FIG. 12. TREK-1 over-expression in CHO cells significantly increases the number of cells in S-phase. CHO cells were transfected with TREK-1 by standard methods and then fixed for cell cycle analysis as described elsewhere. Cells were analyzed by FACS analysis and compared to control CHO cells, TREK-1 expressing cells had a significant shift from G0/G1 to S and G2/M.

Figure 13:
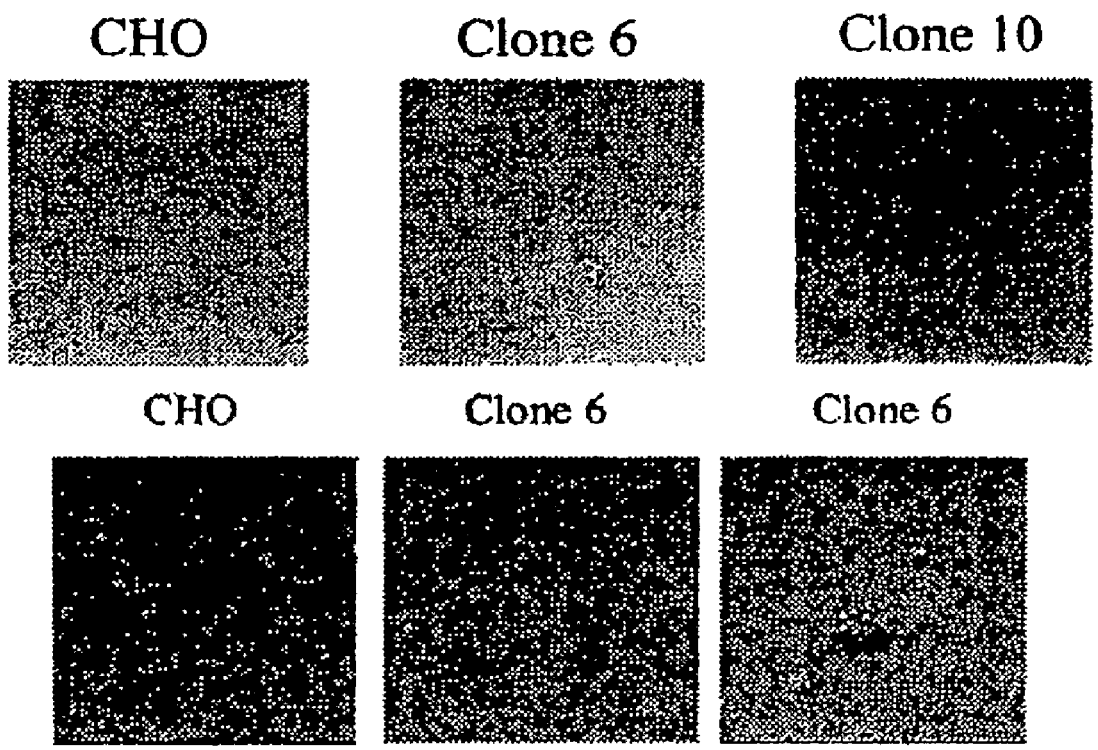

FIG. 13. TREK-1 over-expression in CHO cells promotes anchorage independent growth. Stable TREK-1 over-expressors were tested for growth in soft agar as described elsewhere. Top panel shows the absence of colonies formed by control cells (left) and the presence of many colonies (red spots) formed by clones 6 (middle) and 10 (right). A micrographic analysis of some of these colonies is shown in the bottom panel. Control cells can be seen (left) but these cells, while alive, are not dividing. Over-expressors, however, continue to grow even when suspended in agar and a few examples of colonies formed of many cells are shown (middle and right).

5. DETAILED DESCRIPTION OF THE INVENTION

Described herein is the discovery that the expression of two-pore K+ channels is increased in tumor cells as compared to normal cells. The methods and compositions of the invention may be used for disease diagnosis, drug screening and treatment of cancer. The invention is described in detail in the subsections below.

5.1. Diagnostic Methods

In various embodiments, the present invention provides a variety of methods for the diagnostic and prognostic evaluation of cancer. Such methods may, for example, utilize reagents such as the TREK-1 gene nucleotide sequences and antibodies directed against TREK-1 gene products.

Specifically, such reagents may be used to detect the level of TREK-1 expression, for example, for: (1) the detection of over-expression of TREK-1 gene mRNA relative to normal cells; and/or (2) the detection of an over-abundance of TREK-1 gene product relative to normal cells, each of which correlates with cancer or a progression toward cancer or metastasis.

Thus, the present invention provides a method for diagnosis and/or prognosis of cancer in a subject comprising: (a) detecting the level of TREK-1 expression in a sample derived from a subject; and (b) comparing the level of TREK-1 expression detected in the subject's sample to the level of TREK-1 expression detected in a control sample, wherein an increase in the level of TREK-1 expression detected in the subject's sample as compared to a control sample is an indicator of a subject with cancer or progression toward cancer.

The methods described herein may be applied to samples of cells or cellular materials taken directly from a patient. Any method known in the art for collection or isolation of the desired cells or materials can be used. In particular, for prostate, as well as breast, colon and bladder cancer, samples for testing may be obtained by techniques known in the art.

The methods described herein may be performed, for example, by utilizing pre-packaged diagnostic test kits comprising at least one specific TREK-1 gene nucleic acid or anti-TREK-1 gene product antibody reagent, which may be conveniently used, e.g., in clinical settings or in home settings, to diagnose patients exhibiting preneoplastic or neoplastic abnormalities, and to screen and identify those individuals exhibiting a predisposition to such neoplastic changes.

The present invention is useful for the diagnosis and prognosis of malignant diseases in which the TREK-1 gene or gene product is implicated or is suspected to be implicated. Such malignancies include but are not limited to cancer of the prostate gland, as well as cancer of the breast, colon and bladder. Nucleic acid-based detection techniques are described, below. Peptide detection techniques are described, below.

Expression levels of the TREK-1 gene can be detected by utilizing a number of techniques. For the detection of TREK-1 transcripts, any cell type or tissue in which the TREK-1 gene is expressed, such as, for example, prostate cancer cells, including metastases, may be utilized.

In a preferred embodiment of the invention, quantitative aspects of TREK-1 gene expression are assayed. For example, RNA from a cell type or tissue known, or suspected, to express the TREK-1 gene, such as prostate cancer cells, including metastases, may be isolated and tested utilizing hybridization or PCR techniques. Diagnostic methods for the detection of aberrant TREK-1 gene expression can include hybridization techniques which involve for example, contacting and incubating nucleic acids, including RNA molecules obtained from a sample, e.g., derived from a patient sample, with one or more labeled TREK-1 nucleic acid reagents under conditions favorable for the specific annealing of these reagents to their complementary sequences within the TREK-1 RNA molecule. Preferably, the lengths of these TREK-1 nucleic acid reagents are at least 15 to 30 nucleotides. After incubation, all non-annealed nucleic acids are removed from the nucleic acid:TREK-1 molecule hybrid. The presence of nucleic acids which have hybridized, if any such molecules exist, is then detected. Using such a detection scheme, the nucleic acid from the cell type or tissue of interest can be immobilized, for example, to a solid support such as a membrane, or a plastic surface such as that on a microtitre plate or polystyrene beads. In this case, after incubation, non-annealed, labeled nucleic acid reagents are easily removed. Detection of the remaining, annealed, labeled TREK-1 nucleic acid reagents is accomplished using standard techniques well-known to those in the art. The TREK-1 gene sequences to which the nucleic acid reagents have annealed can be compared to the annealing pattern expected from a normal TREK-1 gene expressing cell in order to determine whether the TREK-1 gene is over-expressed.

In another embodiment of the invention, RT-PCR techniques can be utilized to detect differences in levels of TREK-1 transcripts which may be due to normal or abnormal alternative splicing. TREK-1 nucleic acid sequences may be derived by performing PCR using two oligonucleotide primers designed on the basis of the TREK-1 nucleotide sequences disclosed herein. The template for the reaction may be cDNA obtained by reverse transcription of mRNA prepared from cell lines or tissue known to express TREK-1, i.e, prostate tumor cells.

Mammalian TREK-1 sequences that may be used in the design of hybridization probes and/or PCR primers include, for example, those disclosed in Genebank accession number is NM001017424, Fink et al. (1996, EMBO Journal 15:6854-6862) or Meadows et al., (2000, Pflugers Arch. 439:714-22). The disclosures of these publications in their entireties are hereby incorporated by reference into this application Additionally, it is possible to perform such TREK-1 gene expression assays "in situ", i.e., directly upon tissue sections (fixed and/or frozen) of patient tissue obtained from biopsies or resections, such that no nucleic acid purification is necessary. Nucleic acid reagents such as those described above may be used as probes and/or primers for such in situ procedures (see, for example, Nuovo, G. J., 1992, "PCR In Situ Hybridization: Protocols And Applications", Raven Press, N.Y.).

Antibodies, and fragments thereof, directed against TREK-1 gene product may also be used as diagnostics and prognostics, as described herein. Such diagnostic methods may be used to detect abnormalities in the level of TREK-1 expression. Such antibodies and fragments thereof include, but are not limited to, naturally occurring antibodies, bivalent fragments such as (Fab')$_2$, monovalent fragments such as Fab, single chain antibodies, single chain Fv (scFv), single domain antibodies, multivalent single chain antibodies, diabodies, triabodies, and the like that bind specifically with antigens.

Antibodies, and fragments thereof, to be used in the diagnostic and prognostic methods of the invention are those that bind specifically to an epitope of a mammalian TREK-1 protein. Such TREK-1 proteins include, for example, those having the amino acid sequences disclosed in Genebank accession number is NM 001017424, Fink et al. (1996, EMBO Journal 15:6854-6862) or Meadows et al., (2000, Pflugers Arch. 439:714-22). For the diagnostic and prognostic methods of the invention described below, a directly labeled anti-TREK-1 antibody may be utilized. Alternatively, an unlabeled anti-TREK-1 antibody may be utilized followed by indirect labeling of the antibody with an anti-Ig antibody.

The tissue or cell type to be analyzed will generally include those which are known, or suspected, to express the TREK-1 gene, such as, for example, prostate, breast, colon or bladder cancer cells or metastatic cells. The protein isolation methods employed herein may, for example, be such as those described in Harlow and Lane (Harlow, E. and Lane, D., 1988, "Antibodies: A Laboratory Manual", Cold Spring Harbor Laboratory Press, Cold Spring Harbor, N.Y.), which is incorporated herein by reference in its entirety.

Preferred diagnostic methods for the detection of TREK-1 gene product may involve, for example, immunoassays wherein the TREK-1 gene products are detected by their interaction with an anti-TREK-1 gene product-specific antibody. For example, antibodies, or fragments of antibodies useful in the present invention may be used to quantitatively detect the presence of TREK-1 gene product. The antibodies (or fragments thereof) useful in the present invention may, additionally, be employed histologically, as in immunofluorescence or immunoelectron microscopy, for in situ detection of TREK-1 gene products. In situ detection may be accomplished by removing a histological specimen from a patient, such as paraffin embedded sections of prostate tissue and applying thereto a labeled antibody of the present invention. The antibody (or fragment) is preferably applied by overlaying the labeled antibody (or fragment) onto a biological sample. It may also be desirable to introduce the antibody inside the cell, for example, by making the cell membrane permeable. Through the use of such a procedure, it is possible to determine not only the presence of the TREK-1 gene product but also its distribution in the examined tissue. Using the present invention, those of ordinary skill will readily perceive that any of a wide variety of histological methods (such as staining procedures) can be modified in order to achieve such in situ detection.

Immunoassays for TREK-1 gene product will typically comprise incubating a sample, such as a biological fluid, a tissue extract, freshly harvested cells, or lysates of cells, in the presence of an antibody capable of identifying TREK-1 gene products and detecting the bound antibody by any of a number of techniques well-known in the art.

The biological sample may be brought in contact with and immobilized onto a solid phase support or carrier such as nitrocellulose, or other solid support which is capable of immobilizing cells, cell particles or soluble proteins. The support may then be washed with suitable buffers followed by treatment with the detectably labeled TREK-1 gene specific antibody. The solid phase support may then be washed with the buffer a second time to remove unbound antibody. The amount of bound label on solid support may then be detected by conventional means.

By "solid phase support or carrier" is intended any support capable of binding an antigen or an antibody. Well-known supports or carriers include glass, polystyrene, polypropylene, polyethylene, dextran, nylon, amylases, natural and modified celluloses, polyacrylamides, gabbros, and magnetite. The nature of the carrier can be either soluble to some extent or insoluble for the purposes of the present invention. The support material may have virtually any possible structural configuration so long as the coupled molecule is capable of binding to an antigen or antibody. Thus, the support configuration may be spherical, as in a bead, or cylindrical, as in the inside surface of a test tube, or the external surface of a rod. Alternatively, the surface may be flat such as a sheet, test strip, etc. Preferred supports include polystyrene beads. Those skilled in the art will know many other suitable carriers for binding antibody or antigen, or will be able to ascertain the same by use of routine experimentation.

The binding activity of anti-TREK-1 gene product antibody may be determined according to well known methods. Those skilled in the art will be able to determine operative and optimal assay conditions for each determination by employing routine experimentation.

One of the ways in which the TREK-1 peptide-specific antibody can be detectably labeled is by linking the same to an enzyme and use in an enzyme immunoassay (EIA) (Voller, A., "The Enzyme Linked Immunosorbent Assay (ELISA)", 1978, Diagnostic Horizons 2:1-7, Microbiological Associates Quarterly Publication, Walkersville, Md.); Voller et al., 1978, J. Clin. Pathol. 31:507-520; Butler 1981, Meth. Enzymol. 73:482-523; Maggio, E. (ed.), 1980, Enzyme Immunoassay, CRC Press, Boca Raton, Fla.,; Ishikawa, E. et al., (eds.), 1981, Enzyme Immunoassay, Kgaku Shoin, Tokyo). The enzyme which is bound to the antibody will react with an appropriate substrate, preferably a chromogenic substrate, in such a manner as to produce a chemical moiety which can be detected, for example, by spectrophotometric, fluorimetric or by visual means. Enzymes which can be used to detectably label the antibody include, but are not limited to, malate dehydrogenase, staphylococcal nuclease, delta-5-steroid isomerase, yeast alcohol dehydrogenase, alpha-glycerophosphate dehydrogenase, triose phosphate isomerase, horseradish peroxidase, alkaline phosphatase, asparaginase, glucose oxidase, beta-galactosidase, ribonuclease, urease, catalase, glucose-6-phosphate dehydrogenase, glucoamylase and acetylcholinesterase. The detection can be accomplished by calorimetric methods which employ a chromogenic substrate for the enzyme. Detection may also be accomplished by visual comparison of the extent of enzymatic reaction of a substrate in comparison with similarly prepared standards.

Detection may also be accomplished using any of a variety of other immunoassays. For example, by radioactively labeling the antibodies or antibody fragments, it is possible to detect TREK-1 protein through the use of a radioimmunoassay (RIA) (see, for example, Weintraub, B., Principles of Radioimmunoassays, Seventh Training Course on Radioligand Assay Techniques, The Endocrine Society, March, 1986, which is incorporated by reference herein). The radioactive isotope can be detected by such means as the use of a gamma counter or a scintillation counter or by autoradiography.

It is also possible to label the antibody with a fluorescent compound. When the fluorescently labeled antibody is exposed to light of the proper wavelength, its presence can then be detected due to fluorescence. Among the most commonly used fluorescent labeling compounds are fluorescein isothiocyanate, rhodamine, phycoerythrin, phycocyanin, allophycocyanin, o-phthaldehyde and fluorescamine.

The antibody can also be detectably labeled using fluorescence emitting metals such as $^{152}$Eu, or others of the lanthanide series. These metals can be attached to the antibody using such metal chelating groups as diethylenetriaminepentacetic acid (DTPA) or ethylenediaminetetraacetic acid (EDTA).

The antibody also can be detectably labeled by coupling it to a chemiluminescent compound. The presence of the chemiluminescent-tagged antibody is then determined by detecting the presence of luminescence that arises during the course of a chemical reaction. Examples of particularly useful chemiluminescent labeling compounds are luminol, isoluminol, theromatic acridinium ester, imidazole, acridinium salt and oxalate ester.

Likewise, a bioluminescent compound may be used to label the antibody of the present invention. Bioluminescence is a type of chemiluminescence found in biological systems in, which a catalytic protein increases the efficiency of the chemiluminescent reaction. The presence of a bioluminescent protein is determined by detecting the presence of luminescence. Important bioluminescent compounds for purposes of labeling are luciferin, luciferase and aequorin.

In various embodiments, the present invention provides the measurement of TREK-1 gene product, and the uses of such measurements in clinical applications. The measurement of TREK-1 gene product can be valuable in detecting and/or staging cancer in a subject, in screening of cancer in a population, in differential diagnosis of the physiological condition of a subject, and in monitoring the effect of a therapeutic treatment on a subject In an embodiment of the present invention, measurements of TREK-1 gene expression can be used to stage the cancer in a subject. Staging refers to the grouping of patients according to the extent of their disease. Staging is useful in choosing treatment for individual patients, estimating prognosis, and comparing the results of different treatment programs. Staging of cancer is performed initially on a clinical basis, according to the physical examination and laboratory radiologic evaluation.

Any immunoassay, such as those described above, can be used to measure the amount of TREK-1 gene expression which is compared to a baseline level. This baseline level can be the amount which is established to be normally present in the tissue or body fluid of subjects with various degrees of the disease or disorder. An amount present in the tissue or body fluid of the subject which is similar for detection of the amplified product, the nucleic acid amplification may be performed using radioactively or non-radioactively labeled nucleotides. Alternatively, enough amplified product may be made such that the product may be visualized by standard ethidium bromide staining or by utilizing any other suitable nucleic acid staining method. So a standard amount, established to be normally present in the tissue or body fluid of the subject during a specific stage of cancer, is indicative of the stage of the disease in the subject. The baseline level could also be the level present in the subject prior to the onset of disease or the amount present during remission of the disease.

In specific embodiments of this aspect of the invention, measurements of levels of the TREK-1 gene product can be used in the detection of prostate cancer or the presence of metastases or both. In yet another embodiment of the invention, measurements of levels of the TREK-1 gene product can be used in the detection breast, colon and bladder cancer.

The present invention also provides a method for monitoring the effect of a therapeutic treatment on a subject who has undergone the therapeutic treatment. TREK-1 gene product can be identified and detected in cancer patients with different manifestations of disease, providing a sensitive assay to monitor therapy. The therapeutic treatments which may be evaluated according to the present invention include but are not limited to radiotherapy, surgery, chemotherapy, vaccine administration, endocrine therapy, immunotherapy, and gene therapy, etc.

The method of the invention comprises measuring at suitable time intervals before, during, or after therapy, the amount of a TREK-I gene expression. Any change or absence of change in the amount of the TREK-1 gene expression can be identified and correlated with the effect of the treatment on the subject, such as, for example, a reduction of the transformed phenotype in cancer cells.

In a preferred aspect, the approach that can be taken is to determine the levels of TREK-1 gene expression levels at different time points and to compare these values with a baseline level. The baseline level can be either the level of the marker present in normal, disease free individuals; and/or the levels present prior to treatment, or during remission of disease, or during periods of stability. These levels can then be correlated with the disease course or treatment outcome. Elevated levels. of TREK-1 gene expression relative to the baseline level indicates a poor response to treatment.

5.2. Screening Assays for Compounds that Modulate TREK-1 Activity

The present invention further provides methods for the identification of compounds that may, through their interaction with the TREK-1 gene or TREK-1 gene product, affect the onset, progression and metastatic spread of cancer; especially prostate cancer.

The following assays are designed to identify: (i) compounds that bind to TREK-1 gene products; (ii) compounds that bind to other intracellular proteins that interact with a TREK-1 gene product; and (iii) compounds that modulate the activity of TREK-1 gene (i.e., modulate the level of TREK-1 gene expression and/or modulate the level of TREK-1 gene product activity). Compounds identified via assays such as those described herein may be useful, for example, in elaborating the biological functions of the TREK-1 gene product, and for ameliorating symptoms of cancer. It is to be noted that the compositions of the invention include pharmaceutical compositions comprising one or more of the compounds identified via such methods. Such pharmaceutical compositions can be formulated, for example, as discussed, below.

Assays maybe utilized which identify compounds which bind to TREK-1 gene regulatory sequences (e.g., promoter sequences) and which may modulate the level of TREK-1 gene expression. Such methods for identifying compounds that modulate TREK-1 gene expression, comprise, for example: (a) contacting a test compound with a cell or cell lysate containing a reporter gene operatively associated with a TREK-1 gene regulatory element; and (b) detecting expression of the reporter gene product. Also provided is another method for identifying compounds that modulate TREK-1 gene expression comprising: (a) contacting a test compound with a cell containing TREK-1 transcripts; and (b) detecting the translation of the TREK-1 transcript. Any reporter gene known in the art can be used, such as but not limited to, green fluorescent protein, β-galactosidase, alkaline phosphatase, chloramphenicol acetyltransferase, etc.

In yet another embodiment of the invention, in vitro systems may be designed to identify compounds capable of interacting with, e.g., binding to, the TREK-1 gene product. Such compounds may be useful, for example, in modulating the activity of TREK-1 gene product, in elaborating the biological function of the TREK-1 gene product, or may be utilized in screens for identifying compounds that disrupt normal TREK-1 gene product interactions, or may in themselves disrupt such interactions.

The principle of the assays used to identify compounds that interact with the TREK-1 gene product involves preparing a reaction mixture of the TREK-1 gene product, or fragments thereof and the test compound under conditions and for a time sufficient to allow the two components to interact with, e.g., bind to, thus forming a complex, which can represent a transient complex, which-can be removed and/or detected in the reaction mixture. These assays can be conducted in a variety of ways. For example, one method to conduct such an assay would involve anchoring TREK-1 gene product or the test substance onto a solid phase and detecting TREK-1 gene product/test compound complexes anchored on the solid phase at the end of the reaction. In one embodiment of such a method, the TREK-1 gene product or fragment thereof may be anchored onto a solid surface, and the test compound, which is not anchored, may be labeled, either directly or indirectly.

In yet another embodiment of the invention, displacement assays may be used to identify compounds that interact with the TREK-1 gene product, or fragments thereof. The assay is based on the ability of such compounds to displace or preventing binding of compounds known to interact with the TREK-1 gene product or fragments thereof.

The basic principle of the displacement assay system used to identify compounds that interact with the TREK-1 gene product or fragments thereof involves preparing a reaction mixture containing the TREK-1 gene product, or fragments thereof, and the compound know to bind to TREK-1 under conditions and for a time sufficient to allow the two to interact and bind, thus forming a complex. In order to test a compound for inhibitory activity, the reaction mixture is prepared in the presence and absence of the test compound. The test compound may be initially included in the reaction mixture, or may be added at a time subsequent to the addition of TREK-1 gene product and its intracellular interacting partner. Control reaction mixtures are incubated without the test compound or with a placebo. The formation of any complexes between the TREK-1 gene product or fragments thereof and the compound known to bind to TREK-1 is then detected. The formation of a complex in the control reaction, but not in the reaction mixture containing the test compound, indicates that the compound interferes with the interaction of the TREK-1 gene product and the compound known to bind to TREK-1.

The assay for compounds that interfere with the interaction of the TREK-1 gene product and compounds known to bind to TREK-1 can be conducted in a heterogeneous or homogeneous format. Heterogeneous assays involve anchoring either the TREK-1 gene product or the compound known to bind to TREK-1 onto a solid phase and detecting complexes anchored on the solid phase at the end of the reaction. In homogeneous assays, the entire reaction is carried out in a liquid phase. In either approach, the order of addition of reactants can be varied to obtain different information about the compounds being tested. For example, test compounds that interfere with the interaction between the TREK-1 gene products and the compounds known to bind to TREK-1, e.g., by competition, can be identified by conducting the reaction in the presence of the test substance; i.e., by adding the test substance to the reaction mixture prior to or simultaneously with the TREK-1 gene protein and compound known t bind to TREK-1. Alternatively, test compounds that disrupt preformed complexes, e.g. compounds with higher binding constants that displace one of the components from the complex, can be tested by adding the test compound to the reaction mixture after complexes have been formed.

In a specific embodiment of the invention, compounds know to bind to TREK-1, that may be used in the practice of the invention include, for example, ONO-RS-082, BML263 and BLM 264 (FIG. 9). To facilitate the detection of such compounds, the compounds may be radioactively or fluorescently labeled.

In a specific embodiment of the invention, membrane preparations derived from cells known to express TREK-1, or genetically engineered to express TREK-1, may be used in the displacement assays of the invention. In yet another embodiment of the invention, membrane preparations may be derived from tissues derived from transgenic animals engineered to express TREK-1.

In practice, microtitre plates may conveniently be utilized as the solid phase. The anchored component may be immobilized by non-covalent or covalent attachments. Non-covalent attachment may be accomplished by simply coating the solid surface with a solution of the protein and drying. Alternatively, an immobilized antibody, preferably a monoclonal antibody, specific for the protein to be immobilized may be used to anchor the protein to the solid surface. The surfaces may be prepared in advance and stored.

In order to conduct the assay, the nonimmobilized component is added to the coated surface containing the anchored component. After the reaction is complete, unreacted components are removed (e.g., by washing) under conditions such that any complexes formed will remain immobilized on the solid surface. The detection of complexes anchored on the solid surface can be accomplished in a number of ways. Where the previously nonimmobilized component is pre-labeled, the detection of label immobilized on the surface indicates that complexes were formed. Where the previously nonimmobilized component is not pre-labeled, an indirect label can be used to detect complexes anchored on the surface; e.g., using a labeled antibody specific for the previously nonimmobilized component (the antibody, in turn, may be directly labeled or indirectly labeled with a labeled anti-Ig antibody).

Alternatively, a reaction can be conducted in a liquid phase, the reaction products separated from unreacted components, and complexes detected; e.g., using an immobilized antibody specific for TREK-1 gene product or the test compound to anchor any complexes formed in solution, and a labeled antibody specific for the other component of the possible complex to detect anchored complexes.

In another embodiment of the invention, assays may be utilized to identify intracellular proteins that interact with the TREK-1 gene product. Any method suitable for detecting protein-protein interactions may be employed for identifying TREK-1 protein-intracellular protein interactions. Among the traditional methods which may be employed are co-immunoprecipitation, crosslinking and co-purification through gradients or chromatographic columns. Utilizing procedures such as these allows for the isolation of intracellular proteins which interact with TREK-1 gene product. Once isolated, such an intracellular protein can be identified and can, in turn, be used, in conjunction with standard techniques, to identify additional proteins with which it interacts.

Assays may also be utilized to identify compounds that interfere with TREK-1 gene product/intracellular macromolecular interactions. TREK-1 gene product may, in vivo, interact with one or more intracellular macromolecules, such as proteins and nucleic acid molecules. For purposes of this discussion, such intracellular macromolecules are referred to herein as "interacting partners." Compounds that disrupt TREK-1 interactions in this way may be useful in regulating the activity of the TREK-1 gene product.

The basic principle of the assay systems used to identify compounds that interfere with the interaction between the TREK-1 gene product and its intracellular interacting partner or partners involves preparing a reaction mixture containing the TREK-1 gene product, or fragments thereof, and the interacting partner under conditions and for a time sufficient to allow the two to interact and bind, thus forming a complex. In order to test a compound for inhibitory activity, the reaction mixture is prepared in the presence and absence of the test compound. The test compound may be initially included in the reaction mixture, or may be added at a time subsequent to the addition of TREK-1 gene product and its intracellular interacting partner. Control reaction mixtures are incubated without the test compound or with a placebo. The formation of any complexes between the TREK-1 gene product or fragments thereof and the intracellular interacting partner is then detected. The formation of a complex in the control reaction, but not in the reaction mixture containing the test compound, indicates that the compound interferes with the interaction of the TREK-1 gene product and the interacting partner.

The assay for compounds that interfere with the interaction of the TREK-1 gene product and interacting partners can be conducted in a heterogeneous or homogeneous format. Heterogeneous assays involve anchoring either the TREK-1 gene product or the binding partner onto a solid phase and detecting complexes anchored on the solid phase at the end of the reaction. In homogeneous assays, the entire reaction is carried out in a liquid phase. In either approach, the order of addition of reactants can be varied to obtain different information about the compounds being tested. For example, test compounds that interfere with the interaction between the TREK-1 gene products and the interacting partners, e.g., by competition, can be identified by conducting the reaction in the presence of the test substance; i.e., by adding the test substance to the reaction mixture prior to or simultaneously with the TREK-1 gene protein and intracellular interacting partner. Alternatively, test compounds that disrupt preformed complexes, e.g. compounds with higher binding constants that displace one of the components from the complex, can be tested by adding the test compound to the reaction mixture after complexes have been formed.

In yet another embodiment of the invention, cell-based assays may be used for identification of compounds which modulate TREK-1 activity and which may be used in treating cancer by modulating TREK-1 activity. Specifically, such assays identify compounds which affect TREK-1-dependent processes, such as but not limited to the manifestation of a transformed phenotype, i.e, changes in cell morphology, cell division, differentiation, adhesion, motility, or phosphorylation, dephosphorylation of cellular proteins. Other TREK-1-dependent processes which may be affected include but are not limited to stimulation of K+ channel activity. For example, changes in channel activity may be measured by changes in net current by patch clamp recording or changes in resting membrane potential. Compounds identified via such methods can, for example, be utilized in methods for treating cancer and metastasis.

In an embodiment, cell-based assays are based on expression of the TREK-1 gene product in a mammalian cell and measuring the TREK-1-dependent process. Any mammalian cell that can express the TREK-1 gene and allow the functioning of the TREK-1 gene product can be used, in particular, cancer cells derived from the prostate, such as PC-3 and LNCaP may be used. Other cancer cell lines such as those derived from breast, lung, colon, or other epithelial-derived cancers, may also be used provided that a detectable TREK-1 gene product is produced. Additionally, cells may be recombinantly engineered to express the TREK-1 gene using methods well known to those of skill in the art. In these assays, cells producing functional TREK-1 gene products are exposed to a test compound for an interval sufficient for the compound to modulate the activity of the TREK-1 gene product. The activity of TREK-1 gene product can be measured directly or indirectly through the detection or measurement of TREK-1-dependent cellular processes such as, for example, the manifestation of a transformed phenotype. As a control, a cell not producing the TREK-1 gene product may be used for comparisons. Depending on the cellular process, any techniques known in the art may be applied to detect or measure it.

As disclosed above, over-expression of TREK-1 can result in an increase in cell proliferation. In contrast, decreasing the TREK-1 mediated current may slow proliferation. Accordingly, the present invention provides methods for identifying modulators of TREK-1 activity based on cell proliferation assays. For example, TREK-1 expressing cells may be grown in a 96-well plate and exposed to varying concentrations of a test substance for 4-24 h followed by measurement of cell proliferation.

Cells that may be utilized in the proliferation assays of the invention include cells over-expressing TREK-1 wherein said over-expression results in an increase in cell proliferation. Such cells include cells that naturally over-express TREK-1 as well as cells genetically engineered to overexpress TREK-1. Cells include, for example, PC-3 cells as well as CHO cells transfected with the TREK-1 gene. As demonstrated herein, CHO cells over-expressing TREK-1 have increased proliferation rates and acquire a tumorigenic phenotype, i.e., they exhibit anchorage independent growth. Thus, in a preferred embodiment of the invention genetically engineered CHO cells may be used in the proliferation assays of the invention.

Methods of measuring cell proliferation are well known in the art and most commonly include determining DNA synthesis characteristic of cell replication. There are numerous methods in the art for measuring DNA synthesis, any of which may be used according to the invention. For example, DNA synthesis may be determined using a radioactive label ([$^3$H]thymidine) or labeled nucleotide analogues (BrdU) for detection by immunofluorescence. Alternatively, the rate of proliferation can be measured using any of a number of commercial calorimetric kits, such as the MTT assay. Additionally, the cells may be assayed to determine whether there are changes in levels, or modification, of proteins known to be associated with cell proliferation. Such proteins include, for example, cyclin D1, CDK4 or p107. The efficacy of the test compound can be assessed by generating dose response curves from data obtained using various concentrations of the test compound. A control assay can also be performed to provide a baseline for comparison. Compounds which are found to alter cell proliferation may then be screened in an electrophysiological assay to confirm that the effect is due to modulation of TREK-1.

Using such proliferation assays, non-narcotic analgesics/non-steroidal anti-inflammatory drugs (NSAIDs) were identified as a class of compounds capable of positive modulation of TREK-1 activity. Accordingly, NSAIDs having the following general structure:

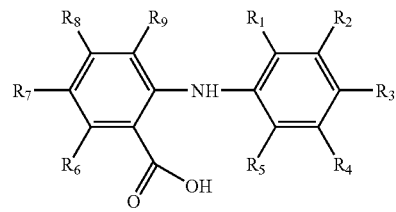

where $R_1$-$R_9$ may be the same or different and are selected from the group consisting of hydrogen, halogen, alkyl, or haloalkyl, may be used to modulate the proliferation of cells. The free —COOH group may also be in the form of a pharmaceutically acceptable salt or ester.

In a specific embodiment of the invention, Meclofenamic acid having the molecular formula $C_{14}H_{11}C_{12}O_2N$ and the following chemical structure:

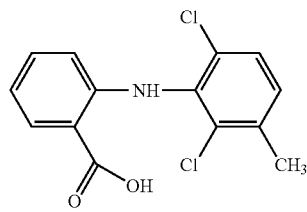

may be used to modulate the activity of TREK-1.

Using proliferation assays, tricyclic antipsychotics were identified as a class of compounds capable of negative modulation of TREK-activity. Accordingly, in an embodiment of the present invention, a TREK-1 inhibitor may be a compound selected from the group consisting of one or more tricyclic antipsychotics, tricyclic antidepressants, thiazines, dibenzoxazepines. In preferred embodiments, the compound is selected from the group consisting of tricyclic thiazines, phenothiazines, thioxanthenes, more preferable from the group consisting of phenothiazines. In one of the more preferred embodiments the TREK-1 inhibitor is the tricyclic antipsychotic phenothiazine Trifluoperazine.

In instances where specific drug use is associated with behavioral effects, the drug may be modified so that it maintains the ability to modulate TREK-1 activity while minimized the CNS effect.

Compounds which may be screened in accordance with the invention include, but are not limited to, small organic or inorganic compounds, peptides, antibodies and fragments thereof, and other organic compounds e.g., peptidomimetics) that modulate TREK-1 activity. Compounds may include, but are not limited to, peptides such as, for example, soluble peptides, including but not limited to members of random peptide libraries (see, eg Lam, K. S. et al., 1991, Nature 354:82-84; Houghten, R. et al., 1991, Nature 354:84-86); and combinatorial chemistry-derived molecular library made of D- and/or L-configuration amino acids, phosphopeptides (including, but not limited to, members of random or partially degenerate, directed phosphopeptide libraries; (see, e.g., Songyang, Z. et al., 1993, Cell 72:767-778), antibodies (including, but not limited to, polyclonal, monoclonal, humanized, anti-idiotypic, chimeric or single chain antibodies, and FAb, F(ab')$_2$ and FAb expression library fragments, and epitope binding fragments thereof), and small organic or inorganic molecules.

5.3. Methods of Treating Proliferative Disorders

Described below are methods and compositions for treating cancer wherein the TREK-1 gene or gene product is used as a therapeutic target. Such compositions include, but are not limited to, peptides, including soluble peptides, small organic or inorganic molecules, therapeutic nucleic acid molecules, including antisense, ribozymes and siNA, all of which function as TREK-1 inhibitors. Additionally, anti-TREK-1 antibodies, or fragments thereof, may be used to treat cancer. Such antibodies and fragments thereof include, but are not limited to, naturally occurring antibodies, bivalent fragments such as (Fab')$_2$, monovalent fragments such as Fab, single chain antibodies, single chain Fv (scFv), single domain antibodies, multivalent single chain antibodies, diabodies, triabodies, and the like that bind specifically with antigens.

The outcome of a treatment is designed to produce in a treated subject a healthful benefit, which in the case of cancer, includes but is not limited to remission of the cancer, palliation of the symptoms of the cancer, control of metastatic spread of the cancer. All such methods involve modulating TREK-1 gene activity and/or expression which in turn modulate the phenotype of the treated cell.

As discussed, above, successful treatment of cancer can be brought about by techniques which serve to decrease TREK-1 activity. Activity can be decreased by, for example, directly decreasing TREK-1 gene product activity and/or by decreasing the level of TREK-1 gene expression. Compounds that may be used to decrease TREK-1 activity include, but are not limited to, oleylamine, sipatrigine or trifluoperazine. Additionally, compounds that inhibit the activity of phospholipase A2 or 15-lipoxygenase (15-LOX) isozymes may be utilized to inhibit the proliferation of cancer cells.

For example, compounds such as those identified through assays described above, which decrease TREK-1 activity, can be used in accordance with the invention to treat cancer. Such compounds can include, but are not limited to peptides, including soluble peptides, and small organic or inorganic compounds, and can be referred to as TREK-1 inhibitors.

It should be understood that compounds capable of modulating TREK-1 activity, as disclosed herein, include functional derivatives and analogs, including pharmaceutically acceptable salts, esters, or hydrates thereof.

In the context of the invention, preference is given to pharmaceutically acceptable salts. "Pharmaceutically acceptable salts" refers to an acid addition salt or a basic addition salt of a compound of the invention in which the resulting counter ion is understood in the art to be generally acceptable for pharmaceutical uses. Pharmaceutically acceptable salts can be salts of the compounds according to the invention with inorganic or organic acids. Preference is given to salts with inorganic acids, such as, for example, hydrochloric acid, hydrobromic acid, phosphoric acid or sulfuric acid, or to salts with organic carboxylic or sulfonic acids, such as, for example, acetic acid, maleic acid, fumaric acid, malic acid, citric acid, tartaric acid, lactic acid, benzoic acid, or methanesulfonic acid, ethanesulfonic acid, phenylsulfonic acid, toluenesulfonic acid or naphthalenedisulfonic acid. Pharmaceutically acceptable salts can also be metal or ammonium salts of the compounds according to the invention. Particular preference is given to, for example, sodium, potassium, magnesium or calcium salts, and also to ammonium salts which are derived from ammonia or organic amines, such as, for example, ethylamine, di- or triethylamine, di- or triethanolamine, dicyclohexylamine, dimethylaminoethanol, arginine, lysine, ethylenediamine or 2-phenylethylamine. (see, Berge et al. *J. Pharm. Sci.* 1977, 66, 1-19.)

The substances according to the invention may also be present as pharmaceutically acceptable ester, such as the methyl ester, ethyl ester and the like.

When one or more chiral centers are present in the compounds of the present invention, the individual isomers and mixtures thereof (e.g., racemates, etc.) are intended to be encompassed by the formulae depicted herein. In certain embodiments, compounds of the invention may exist in several tautomeric forms. Accordingly, the chemical structures depicted herein encompass all possible tautomeric forms of the illustrated compounds. Compounds of the invention may exist in various hydrated forms.

In an embodiment of the invention, the level of TREK-1 expression can be modulated using TREK-1 based oligpnucleotide molecules including but not limited to antisense, ribozyme, or RNAi approaches to inhibit or prevent translation of TREK-1 mRNA transcripts or triple helix approaches to inhibit transcription of the TREK-1 gene (herein after referred to as "therapeutic nucleic acid molcules"). Antisense, RNAi and ribozyme approaches involve the design of oligonucleotides (either DNA or RNA) that are complementary to TREK-1 mRNA. The antisense, siNA or ribozyme oligonucleotides will be targeted to complementary TREK-1 mRNA transcripts and prevent translation. Absolute complementarity, although preferred, is not required. One skilled in the art can ascertain a tolerable degree of mismatch by use of standard procedures to determine the melting point of the hybridized complex. Mammalian TREK-1 sequences that may be used in the design of antisense, RNAi and ribozymes include those disclosed in Genebank accession number is NM001017424, Fink et al. (1996, EMBO Journal 15:6854-6862) or Meadows et al., (2000, Pflugers Arch. 439:714-22).

In a preferred embodiment of the invention, double-stranded short interfering nucleic acid (siNA) molecules may be designed to inhibit TREK-1 expression. In one embodiment, the invention features a double-stranded siNA molecule that down-regulates expression of the TREK-1 gene product, wherein said siNA molecule comprises about 15 to about 28 base pairs.

In one embodiment, the invention features a double stranded short interfering nucleic acid (siNA) molecule that directs cleavage of a TREK-1 RNA via RNA interference (RNAi), wherein the double stranded siNA molecule comprises a first and a second strand, each strand of the siNA molecule is about 18 to about 28 nucleotides in length, the first strand of the siNA molecule comprises nucleotide sequence having sufficient complementarity to the TREK-1 RNA for the siNA molecule to direct cleavage of the TREK-1 RNA via RNA interference, and the second strand of said siNA molecule comprises nucleotide sequence that is complementary to the first strand.

The use of antisense molecules as inhibitors of gene expression is a specific, genetically based therapeutic approach (for a review, see Stein, in Ch. 69, Section 5 "Cancer: Principle and Practice of Oncology", 4th ed., ed. by DeVita et al., J. B. Lippincott, Philadelphia 1993). The present invention provides the therapeutic use of nucleic acids of at least six nucleotides that are antisense to the TREK-1 gene or a portion thereof. An "antisense" TREK-1 nucleic acid as used herein refers to a nucleic acid capable of hybridizing to a portion of a TREK-1 RNA (preferably niRNA) by virtue of some sequence complementarity.

The antisense nucleic acid of the invention may be complementary to a coding and/or noncoding region of a TREK-1 mRNA. The antisense molecules will bind to the complementary TREK-1 gene mRNA transcripts and reduce or prevent translation. Absolute complementarity, although preferred, is not required. A sequence "complementary" to a portion of an RNA, as referred to herein, means a sequence having sufficient complementarity to be able to hybridize with the RNA, forming a stable duplex; in the case of double-stranded antisense nucleic acids, a single strand of the duplex DNA may thus be tested, or triplex formation may be assayed. The ability to hybridize will depend on both the degree of complementarity and the length of the antisense nucleic acid. Generally, the longer the hybridizing nucleic acid, the more base mismatches with an RNA it may contain and still form a stable duplex (or triplex, as the case may be). One skilled in the art can ascertain a tolerable degree of mismatch by use of standard procedures to determine the melting point of the hybridized complex.

In yet another embodiment of the invention, ribozyme molecules designed to catalytically cleave TREK-1 mRNA transcripts can also be used to prevent translation of TREK-1 MRNA and expression of TREK-1. (See, e.g., PCT International Publication WO90/11364, published Oct. 4, 1990; Sarver et al., 1990, Science 247:1222-1225).

Ribozymes are enzymatic RNA molecules capable of catalyzing the specific cleavage of RNA (For a review see, for example Rossi, J., 1994, Current Biology 4:469-471). The mechanism of ribozyme action involves sequence specific hybridization of the ribozyme molecule to complementary target RNA, followed by an endonucleolytic cleavage. The composition of ribozyme molecules must include one or more sequences complementary to the target gene MRNA, and must include the well known catalytic sequence responsible for mRNA cleavage. For this sequence, see U.S. Pat. No. 5,093,246, which is incorporated by reference herein in its entirety. As such, within the scope of the invention are engineered hammerhead motif ribozyme molecules that specifically and efficiently catalyze endonucleolytic cleavage of RNA sequences encoding target gene proteins.

Ribozyme molecules designed to catalytically cleave TREK-1 gene mRNA transcripts can also be used to prevent translation of TREK-1 gene mRNA and expression of target or pathway gene. (See, e.g., PCT International Publication WO90/11364, published Oct. 4, 1990; Sarver et al., 1990, Science 247:1222-1225). While ribozymes that cleave MRNA at site specific recognition sequences can be used to destroy TREK-1 gene mRNAs, the use of hammerhead ribozymes is preferred. Hammerhead ribozymes cleave mRNAs at locations dictated by flanking regions that form complementary base pairs with the target mRNA. The sole requirement is that the target mRNA have the following sequence of two bases: 5'-UG-3'. The construction and production of hammerhead ribozymes is well known in the art and is described more fully in Haseloff and Gerlach, 1988, Nature, 334:585-591. Preferably the ribozyme is engineered so that the cleavage recognition site is located near the 5' end of the TREK-1 gene mRNA; i.e., to increase efficiency and minimize the intracellular accumulation of non-functional mRNA transcripts.

The ribozymes of the present invention also include RNA endoribonucleases (hereinafter "Cech-type ribozymes") such as the one which occurs naturally in *Tetrahymena thermophila* (known as the IVS, or L-19 IVS RNA) and which has been extensively described by Thomas Cech and collaborators (Zaug, et al., 1984, Science, 224:574-578; Zaug and Cech, 1986, Science, 231:470-475; Zaug, et al., 1986, Nature, 324:429-433; published International patent application No. WO 88/04300 by University Patents Inc.; Been and Cech, 1986, Cell, 47:207-216). The Cech-type ribozymes have an eight base pair active site which hybridizes to a target RNA sequence whereafter cleavage of the target RNA takes place. The invention encompasses those Cech-type ribozymes which target eight base-pair active site sequences that are present in a TREK-1 gene.

Alternatively, endogehous TREK-1 gene expression can be reduced by targeting deoxyribonucleotide sequences complementary to the regulatory region of the TREK-1 gene (i.e., the TREK-1 promoter and or enhancer) to form triple helical structures that prevent transcription of the TREK-1 gene in targeted tumor cells in the body. (See generally, Helene, C. et al., 1991, Anticancer Drug Des. 6:569-584 and Maher, L J, 1992, Bioassays 14:807-815).

Therapeutic nucleic acid molecules such as RNAi, antisense and ribozyme molecules which inhibit TREK-1 gene expression can be used in accordance with the invention to reduce the level of TREK-1 gene expression, thereby effectively reducing the level of TREK-1 activity. Still further, triple helix molecules can be utilized in reducing the level of TREK-1 gene activity.

Such therapeutic nucleic acid molecules, i.e., RNAi, antisense, ribozyme and triple helix forming oligonucleotides, may be synthesized using standard methods known in the art for the synthesis of DNA and RNA molecules. These include techniques for chemically synthesizing oligodeoxyribonucleotides and oligoribonucleotides, such as for example, solid phase phosphoramidite chemical synthesis. The nucleic acid molecule can be DNA or RNA or chimeric mixtures or derivatives or modified versions thereof, single-stranded or double-stranded. The nucleic acid molecule can be modified at the base moiety, sugar moiety, or phosphate backbone, for example, to improve stability of the molecule, hybridization, etc. The nucleic acid molecule may include other appended groups such as peptides (e.g., for targeting host cell receptors in vivo), or agents facilitating transport across the cell membrane (see, e.g., Letsinger et al., 1989, Proc. Natl. Acad. Sci. U.S.A. 86:6553-6556; Lemaitre et al., 1987, Proc. Natl. Acad.

Sci. 84:648-652; PCT Publication No. WO88/09810, published Dec. 15, 1988), hybridization-triggered cleavage agents. (See, e.g., Krol et al., 1988, BioTechniques 6:958-976) or intercalating agents. (See, e.g., Zon, 1988, Pharm. Res. 5:539-549). To this end, the nucleic acid molecules may be conjugated to another molecule, e.g., a peptide, hybridization triggered cross-linking agent, transport agent, hybridization-triggered cleavage agent, etc.

Alternatively, the therapeutic nucleic acid molecules can be generated by in vitro and in vivo transcription of DNA sequences encoding the therapeutic nucleic acid molecules. Such DNA sequences can be incorporated into a wide variety of vectors which incorporate suitable RNA polymerase promoters such as the T7 or SP6 polymerase promoters.

Any technique which serves to selectively administer nucleic acid molecules to a cell population of interest can be used, for example, by using a delivery complex. Such a delivery complex can comprise an appropriate nucleic acid molecule and a targeting means. Such targeting means can comprise, for example, sterols, lipids, viruses or target cell specific binding agents. In a specific embodiment, pharmaceutical compositions comprising a therapeutic nucleic acid molecule are administered via biopolymers, liposomes, microparticles, or microcapsules. In various embodiments of the invention, it may be useful to use such compositions to achieve sustained release of the therapeutic nucleic acids. In a specific embodiment, it may be desirable to utilize liposomes targeted via antibodies to specific identifiable tumor antigens (Leonetti et al., 1990, Proc. Natl. Acad. Sci. U.S.A. 87:2448-2451; Renneisen et al., 1990, J. Biol. Chem. 265: 16337-16342).

It is often difficult to achieve intracellular concentrations of the therapeutic nucleic acid molecule sufficient to suppress translation of endogenous mRNAs. Therefore, a preferred approach utilizes a recombinant DNA construct in which expression of the therapeutic nucleic acid molecule is placed under the control of a strong pol III or pol II promoter. For general reviews of the methods of gene therapy, see Goldspiel et al., 1993, Clinical Pharmacy 12:488-505; Wu and Wu, 1991, Biotherapy 3:87-95; Tolstoshev, 1993, Ann. Rev. Pharmacol. Toxicol. 32:573-596; Mulligan, 1993, Science 260:926-932; and Morgan and Anderson, 1993, Ann. Rev. Biochem. 62:191-217; May, 1993, TIBTECH 11(5):155-215). Methods commonly known in the art of recombinant DNA technology which can be used are described in Ausubel et al. (eds.), 1993, Current Protocols in Molecular Biology, John Wiley & Sons, NY; Kriegler, 1990, Gene Transfer and Expression, A Laboratory Manual, Stockton Press, NY; and in Chapters 12 and 13, Dracopoli et al. (eds.), 1994, Current Protocols in Human Genetics, John Wiley & Sons, NY.

The use of recombinant DNA constructs to transfect target cells in the patient will result in the transcription of sufficient amounts of the therapeutic nucleic acid molecule that will form complementary base pairs with the endogenous TREK-1 gene transcripts and thereby prevent translation of the TREK-1 gene mRNA. For example, a vector can be introduced in vivo such that it is taken up by a cell and directs the transcription of an antisense RNA. Such a vector can remain episomal or become chromosomally integrated, as long as it can be transcribed to produce the desired antisense RNA.

Such vectors can be constructed by recombinant DNA technology methods standard in the art. Vectors can be plasmid, viral, or others known in the art, used for replication and expression in mammalian cells. Expression of the sequence encoding a therapeutic nucleic acid can be by any promoter known in the art to act in mammalian, preferably human cells. Such promoters can be inducible or constitutive. Such promoters include but are not limited to: the SV40 early promoter region (Bemoist and Chambon, 1981, Nature 290:304-310), the promoter contained in the 3' long terminal repeat of Rous sarcoma virus (Yamamoto et al., 1980, Cell 22:787-797), the herpes thymidine kinase promoter (Wagner et al., 1981, Proc. Natl. Acad. Sci. U.S.A. 78:1441-1445), the regulatory sequences of the metallothionein gene (Brinster et al., 1982, Nature 296:39-42), etc. Any type of plasmid, cosmid, YAC or viral vector can be used to prepare the recombinant DNA construct which can be introduced either directly into the tissue site, or via a delivery complex. Alternatively, viral vectors can be used which selectively infect the desired tissue.

In a specific embodiment, a viral vector that contains the nucleic acid of interest, i.e., a therapeutic nucleic acid molecule is used. For example, a retroviral vector can be used (see Miller et al., 1993, Meth. Enzymol. 217:581-599). These retroviral vectors have been modified to delete retroviral sequences that are not necessary for packaging of the viral genome and integration into host cell DNA. The TREK-1 nucleic acid to be used in gene therapy is cloned into the vector, which facilitates delivery of the gene into a patient. More detail about retroviral vectors can be found in Boesen et al., 1994, Biotherapy 6:291-302, which describes the use of a retroviral vector to deliver the mdrl gene to hematopoietic stem cells in order to make the stem cells more resistant to chemotherapy. Other references illustrating the use of retroviral vectors in gene therapy are: Clowes et al., 1994, J. Clin. Invest. 93:644-651; Kiem et al., 1994, Blood 83:1467-1473; Salmons and Gunzberg, 1993, Human Gene Therapy 4:129-141; and Grossman and Wilson, 1993, Curr. Opin. in Genetics and Devel. 3:110-114.

Adenoviruses are other viral vectors that can be used in gene therapy. Adenoviruses are especially attractive vehicles for delivering genes to respiratory epithelia. Adenoviruses naturally infect respiratory epithelia where they cause a mild disease. Other targets for adenovirus-based delivery systems are liver, the central nervous system, endothelial cells, and muscle. Adenoviruses have the advantage of being capable of infecting non-dividing cells. Kozarsky and Wilson, 1993, Current Opinion in Genetics and Development 3:499-503 present a review of adenovirus-based gene therapy. Bout et al., 1994, Human Gene Therapy 5:3-10 demonstrated the use of adenovirus vectors to transfer genes to the respiratory epithelia of rhesus monkeys. Other instances of the use of adenoviruses in gene therapy can be found in Rosenfeld et al., 1991, Science 252:431-434; Rosenfeld et al., 1992, Cell 68:143-155; and Mastrangeli et al., 1993, J. Clin. Invest. 91:225-234. Adeno-associated virus (AAV) has also been proposed for use in gene therapy (Walsh et al., 1993, Proc. Soc. Exp. Biol. Med. 204:289-300.

Alternatively, mesenchymal stem cells which express gap junctional protein may be genetically engineered to express the therapeutic nucleic acid of interest followed by transplantation into tumor tissue, i.e, prostate tumor tissue. It has been demonstrated that siRNA, for example, can cross gap junctional channels to affect the function of target cells (Valiunas et al., 2005, J. Physiol. (Lond) 568:459-468).

In another embodiment of the invention, nucleic acid molecules comprising a sequence encoding a dominant negative mutant TREK-1 protein or non-functional fragment or derivative thereof, are administered to inhibit TREK-1 function. The TREK-1 channel is normally found in the cell as a homodimer. When a dominant-negative mutant TREK-1 protein is overexpressed it forms a heterodimer with the endogenous wild-type monomers resulting in a non-functional channel. Thus, dominant negative TREK-1 mutants are those mutants that are defective in function but effective in binding to form heterodimers with the wild type TREK-1. Specifically, the nucleic acid comprises a TREK-1 nucleic acid that is part of an expression vector that expresses a dominant non-functional TREK-1 protein or fragment or chimeric protein thereof in cancer cells. In a specific embodiment of the invention, a dominant negative TREK-1 can be created by mutating a key residue in the ion selectivity filter in both pore-forming loops (G161E and G268E). Dominant non-functional TREK-1 can be engineered for expression in cancer cells that inappropriately overexpress TREK-1.

The present invention is directed to a method of modulating cell proliferation comprising contacting a cell with a composition comprising a nucleic acid sequence, wherein the nucleotide sequence encodes a variant TREK-1 that has dominant negative activity. In a specific embodiment, the nucleic acid encoding the dominant negative mutant TREK-1 is directly administered in vivo, where it is expressed to produce the non-functional TREK-1 gene product. This can be accomplished using any of the gene therapy methods described above for in vivo expression of therapeutic nucleic acid molecules.

The form and amount of therapeutic nucleic acid envisioned for use depends on the cancer, desired effect, patient state, etc., and can be determined by one skilled in the art.

Antibodies exhibiting capability to down regulate TREK-1 gene product activity can also be utilized to treat cancer. Such antibodies can be generated using standard techniques. Such antibodies include but are not limited to polyclonal, monoclonal, Fab fragments, single chain antibodies, chimeric antibodies, and the like.

5.4. Pharmaceutical Preparations and Methods of Administration

The compounds and nucleic acid sequences described herein can be administered to a patient at therapeutically effective doses to treat or prevent cancer. A therapeutically effective dose refers to that amount of a compound sufficient to result in a healthful benefit in the treated subject.

Toxicity and therapeutic efficacy of compounds can be determined by standard pharmaceutical procedures in cell cultures or experimental animals, e.g., for determining the $LD_{50}$ (the dose lethal to 50% of the population) and the $ED_{50}$ (the dose therapeutically effective in 50% of the population). The dose ratio between toxic and therapeutic effects is the therapeutic index and it can be expressed as the ratio $LD_{50}/ED_{50}$. Compounds which exhibit large therapeutic indices are preferred. While compounds that exhibit toxic side effects can be used, care should be taken to design a delivery system that targets such compounds to the site of affected tissue in order to minimize potential damage to uninfected cells and, thereby, reduce side effects.

The data obtained from the cell culture assays and animal studies can be used in formulating a range of dosage for use in humans. The dosage of such compounds lies preferably within a range of circulating concentrations that include the $ED_{50}$ with little or no toxicity. The dosage can vary within this range depending upon the dosage form employed and the route of administration utilized. For any compound used in the method of the invention, the therapeutically effective dose can be estimated initially from cell culture assays. A dose can be formulated in animal models to achieve a circulating plasma concentration range that inhibits TREK-1 by 50% as determined in cell culture. Such information can be used to more accurately determine useful doses in humans. Levels in plasma can be measured, for example, by high performance liquid chromatography.

Pharmaceutical compositions for use in accordance with the present invention can be formulated in conventional manner using one or more physiologically acceptable carriers or excipients. Thus, the compounds and their physiologically acceptable salts and solvents can be formulated for administration by inhalation or insufflation (either through the mouth or the nose) or oral, buccal, parenteral or rectal administration. In a specific embodiment of the invention, the pharmaceutical compositions of the invention may be implanted directly into, or in close proximity, to the tumor tissue. For example, the pharmaceutical compositions may be implanted into the prostate, thereby, allowing the administration of higher doses of drug to a more limited tissue area. Such compositions may be formulated into a form that allows for sustained release of the drug in the area to be treated.

For oral administration, the pharmaceutical compositions can take the form of, for example, tablets or capsules prepared by conventional means with pharmaceutically acceptable excipients such as binding agents (e.g., pregelatinised maize starch, polyvinylpyrrolidone or hydroxypropyl methylcellulose); fillers (e.g., lactose, microcrystalline cellulose or calcium hydrogen phosphate); lubricants (e.g., magnesium stearate, talc or silica); disintegrants (e.g., potato starch or sodium starch glycolate); or wetting agents (e.g., sodium lauryl sulphate). The tablets can be coated by methods well known in the art. Liquid preparations for oral administration can take the form of, for example, solutions, syrups or suspensions, or they can be presented as a dry product for constitution with water or other suitable vehicle before use. Such liquid preparations can be prepared by conventional means with pharmaceutically acceptable additives such as suspending agents (e.g., sorbitol syrup, cellulose derivatives or hydrogenated edible fats); emulsifying agents (e.g., lecithin or acacia); non-aqueous vehicles (e.g., almond oil, oily esters, ethyl alcohol or fractionated vegetable oils); and preservatives (e.g., methyl or propyl-p-hydroxybenzoates or sorbic acid). The preparations can also contain buffer salts, flavoring, coloring and sweetening agents as appropriate.

Preparations for oral administration can be suitably formulated to give controlled release of the active compound. For buccal administration the compositions can take the form of tablets or lozenges formulated in conventional manner.

For administration by inhalation, the compounds for use according to the present invention are conveniently delivered in the form of an aerosol spray presentation from pressurized packs or a nebulizer, with the use of a suitable propellant, e.g., dichlorodifluoromethane, trichlorofluoromethane, dichlorotetrafluoroethane, carbon dioxide or other suitable gas. In the case of a pressurized aerosol the dosage unit can be determined by providing a valve to deliver a metered amount. Capsules and cartridges of e.g. gelatin for use in an inhaler or insufflator can be formulated containing a powder mix of the compound and a suitable powder base such as lactose or starch.

The compounds can be formulated for parenteral administration (i.e., intravenous or intramuscular) by injection, via, for example, bolus injection or continuous infusion. Formulations for injection can be presented in unit dosage form, e.g., in ampoules or in multi-dose containers, with an added preservative. The compositions can take such forms as suspensions, solutions or emulsions in oily or aqueous vehicles, and can contain formulatory agents such as suspending, stabilizing and/or dispersing agents. Alternatively, the active ingredient can be in powder form for constitution with a suitable vehicle, e.g., sterile pyrogen-free water, before use.

The compounds can also be formulated in rectal compositions such as suppositories or retention enemas, e.g., containing conventional suppository bases such as cocoa butter or other glycerides.

In addition to the formulations described previously, the compounds can also be formulated as a depot preparation. Such long acting formulations can be administered by implantation (for example subcutaneously or intramuscularly) or by intramuscular injection. Thus, for example, the compounds can be formulated with suitable polymeric or hydrophobic materials (for example as an emulsion in an acceptable oil) or ion exchange resins, or as sparingly soluble derivatives, for example, as a sparingly soluble salt.

6. EXAMPLE

Two-Pore Domain K+ Channels are Over-Expressed in Cancer

Initial studies of prostate epithelium have identified expression of the TREK-1 two pore channel in two prostate cancer cell lines, PC-3 and LNCaP but not in normal prostate epithelial cells (NPE; FIG. 1). Expression of functional channels in both PC-3 (FIG. 2, Panel A) and LNCaP (data not shown) cells has been confirmed by whole-cell patch-clamp recording in the voltage-clamp configuration. TREK-1 was identified in these recordings as the sipatrigine-sensitive current in the presence of CsCl (5 MM), TEA (10 mM) and nifedipine (5 μM) which were are added to block other K⁺ and the $I_{CaL}$ currents. Normal prostate epithelial cells do not express any TREK-1 current under these conditions (see FIG. 4, below). In addition, a TREK-1 channel mutant has been created which is disrupted in the selectivity filter of the pore region (G161E/G268E). This mutant channel carries no current when expressed in CHO cells and functions as a dominant-negative (dn-TREK) when co-expressed with wild-type channel. Transfection of PC-3 cells with dn-TREK (FIG. 2, Panel B) leads to complete ablation of endogenous TREK-1 current.

Additional studies have identified the presence of TASK-1 (identified as a methanandamide-sensitive current) (Maingret et al., 2001) and TASK-3 (identified as a ruthenium red-sensitive current) (Czirjak and Enyedi, 2003) in both LNCaP and PC-3 cells.

Since TREK-1 is expressed in the prostate cancer cells but not in NPE, such data indicates that TREK-1 might contribute to the rapid proliferation rate of prostate cancer cells. To confirm this hypothesis, the proliferation of untransfected PC-3 cells was compared with cells that were transfected either with the dominant-negative TREK-1 or an empty vector (pEGFP). The cells which over-express the dn-TREK carry no TREK-1 current (see FIG. 2, Panel B). Proliferation rate was determined using a standard calorimetric assay (Cell Proliferation Kit I [MTT]; Roche) and normalized to the proliferation rate of untransfected PC-3. pEGFP transfection does not affect the proliferation rate of PC-3 cells. However, over-expression of dn-TREK significantly slows the proliferation rate by 44±6.6% (FIG. 3; n=6). It should be noted that the transfection efficiency in these experiments is approximately 30%. While this is not an issue for the electrophysiology experiments where cells expressing the dominant-negative channel can be individually selected due to the co-expression of EGFP, the efficiency should be expected to reduce the effect observed in the proliferation assay which measures the rate of all the cells in the microplate. Therefore, the 47% inhibition is believed to be an underestimate of the effect.

Figure 4:
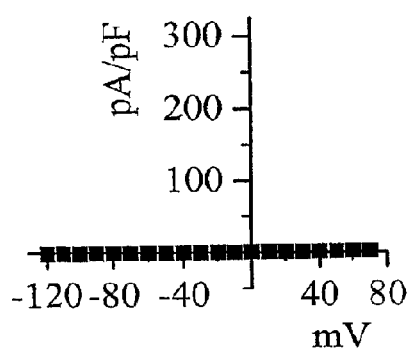
Figure 4:
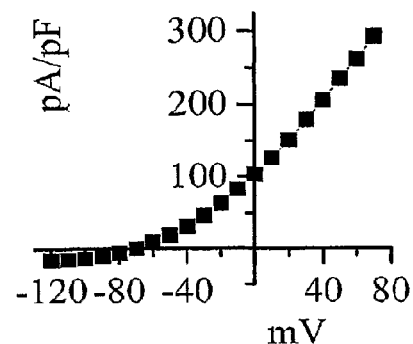
Figure 4:
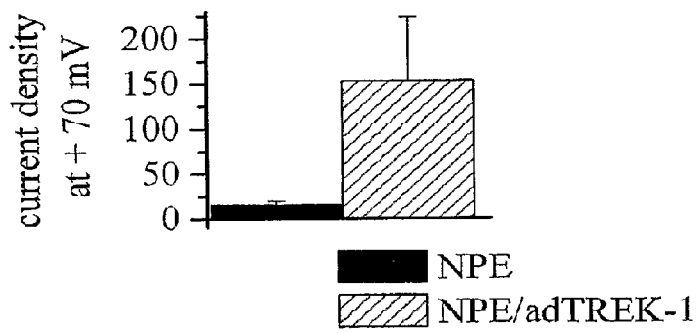

To test whether over-expression of TREK-1 in normal prostate epithelial cells would increase the proliferative rate experiments were conducted with a TREK-1 bearing adenovirus. Normal prostate epithelial cells do not exhibit TREK-1 current (FIG. 4, Panel A). However, when NPE are infected with the TREK-1 virus a large current is readily detected (FIG. 4, Panel B). The effect of this current on the proliferation rate in NPE was tested and it was determined that expression of TREK-1 significantly increased the proliferation rate of NPE by 270±27.7% (FIG. 5, n=5, p<0.05).

As demonstrated in FIG. 5, expression of TREK-1 increases proliferation of normal prostate epithelial cells (NPE). Normal prostate epithelial cell cultures were obtained from Clonetics and infected with a TREK-1-containing adenovirus. Some virally infected cells were also treated with sipatrigine (10 μM), a TREK-1 blocker. Cell proliferation was assessed using the MTT assay as described in FIG. 3. These data are presented as mean±SEM from five paired experiments. * p<0.05, the NPE/TREK-1 group differed significantly from each of the other treatments and no other groups were different.

FIG. 6 demonstrates, by immunohistochemical staining of human prostate tissue, that TREK-1 is over-expressed in cancer. Human tissue samples were stained with rabbit polyclonal anti-human TREK-1 antibody (Alomone). Panels A and B show a low power and high power view of the same field. Under the low power, a normal gland is visible (center right). The epithelial cells lining the luminal surface are very lightly stained. An adjacent cancerous gland (center left) shows a very small luminal space and the epithelial cells lining it are very densely stained indicating an overexpression of TREK-1. The same features are visible under higher power in Panel B.

FIG. 7 reveals that Meclofenamate activates TREK-1 current in CHO cells that heterologously express the channel. CHO cells were transfected with a plasmid encoding human TREK-1 and the current was studied by patch clamp. The current-voltage relation was determined using a ramp protocol that went from −130 mV to +40 mV in 6 s (after correction for the junction potential). Current was greater in the presence of meclofenamate. This is typical of 7 cells.

Further, FIG. 8 reveals that Trifluoperazine inhibits TREK-1 current in CHO cells that heterologously express the channel. CHO cells were transfected with a plasmid encoding human TREK-1 and the current was studied by patch clamp. The current-voltage relation was determined using a ramp protocol that went from −130 mV to +40 mV in 6 s (after correction for the junction potential). Current was less in the presence of trifluoperazine. This is typical of 3 cells.

Transiently transfected CHO cells (obtained through ATCC) were fixed with 1 ml ice-cold 70% ethanol 48 h after transfection with TREK-1. Fixation was followed by RNase treatment and staining with propidium iodide (50 μg/ml). Stained samples were analyzed on a FACScan flow cytometer and data were analyzed using Cell Quest software to assess the cell-cycle distribution patterns. FIGS. 10-12 demonstrate that TREK-1 CHO stable over-expressor cell lines have significantly higher proliferation rates which correlate with the TREK-1 current.

Anchorage-independent growth of stably transfected CHO cells was also measured. Creation of the TREK-1 stable over-expressing lines was done in CHO cells using zeocin selection. CHO cells that stably over-expressed TREK-1 (1×10⁶ cells/well) were suspended in 0.4% agar with complete RPMI medium in six well plates. Twenty days later the plates were stained with iodonitrotetrazolium chloride for 6 h. Colonies were scored using a light microscope at ×10 magnification.

As demonstrated in FIG. 13, TREK-1 over-expression promotes anchorage-independent growth.

The present invention is not to be limited in scope by the specific embodiments described herein which are intended as single illustrations of individual aspects of the invention, and functionally equivalent methods and components are within the scope of the invention. Indeed, various modifications of the invention, in addition to those shown and described herein will become apparent to those skilled in the art from the foregoing description and accompanying drawings. Such modifications are intended to fall within the scope of the claims. Throughout this application various publications are referenced. The disclosures of these publications in the entireties are hereby incorporated by reference into this application in order to more fully describe the state of the art to those skilled therein as of the date of the invention described and claimed herein.

We claim:

1. A method of reducing proliferation of cancer cells over-expressing TREK-1, comprising contacting the cancer cell with a nucleic acid sequence encoding a dominant negative TREK-1 ion selectivity filter.

2. The method of claim 1 wherein the cancer is selected from the group comprising prostate cancer, bladder cancer, breast cancer, and colon cancer.

* * * * *